(12) United States Patent
Bouquet

(10) Patent No.: US 12,733,803 B2
(45) Date of Patent: Sep. 15, 2026

(54) VAGINAL SPECULUM AND CERVICAL SCREENING KIT

(71) Applicant: Viospex, Parker, CO (US)

(72) Inventor: Jean Bouquet, Parker, CO (US)

(73) Assignee: Viospex, Parker, CO (US)

( * ) Notice: Subject to any disclaimer, the term of this patent is extended or adjusted under 35 U.S.C. 154(b) by 191 days.

(21) Appl. No.: 18/056,129

(22) Filed: Nov. 16, 2022

(65) Prior Publication Data

US 2023/0148856 A1 May 18, 2023

Related U.S. Application Data

(60) Provisional application No. 63/280,438, filed on Nov. 17, 2021.

(51) Int. Cl.

| | |
|---|---|
| ***A61B 1/32*** | (2006.01) |
| ***A61B 1/00*** | (2006.01) |
| ***A61B 1/303*** | (2006.01) |
| ***A61M 29/00*** | (2006.01) |

(52) U.S. Cl.
CPC ............ *A61B 1/32* (2013.01); *A61B 1/00016* (2013.01); *A61B 1/303* (2013.01); *A61M 29/00* (2013.01)

(58) Field of Classification Search
CPC .......... A61B 1/303; A61B 1/32; A61B 5/6898
See application file for complete search history.

(56) References Cited

U.S. PATENT DOCUMENTS

| | | | | |
|---|---|---|---|---|
| 2013/0023914 A1* | 1/2013 | Truong | .................. | A61B 1/015 606/162 |
| 2020/0297205 A1* | 9/2020 | Hill | .......................... | A61B 1/24 |

* cited by examiner

*Primary Examiner* — Julianna N Harvey
(74) *Attorney, Agent, or Firm* — Davis Graham & Stubbs LLP

(57) ABSTRACT

A vaginal speculum, conical in shape, made out of clear plastic resin or metal that when closed can easily and gently be inserted into the introitus (vaginal opening). In certain embodiments, a dilator is used to introduce and/or expand the speculum. Various mechanisms are disclosed for dilating the speculum, after it has been inserted, so as to allow inspection of the patient's cervix. Such dilation can be affected relative to multiple axes, or even in substantially continuous, radial fashion about the periphery of the speculum, for improved visualization. In addition, the speculum may include a mount for mounting auxiliary equipment for simplified handling. Such auxiliary equipment may include imaging elements, electrosurgical equipment, and smoke evacuation equipment, among other things. Associated processing equipment enables processing of image information locally or remotely via a data network.

9 Claims, 37 Drawing Sheets

110
$D_2$
100
112
$D_1$
120
114
106
104
102

108
107
104
Z
Y
X
106
114
100
124
114
116

102
118
122

D2
314
L1
305

302
D1
300
312
D1
310
L2
304
306
308

D2
314
L1
305
D1
D1
310
L2
306
308

D2
314
302
L1
305
L3
313
310
L2
304
306

D2
314
302
L1
305
L3
313
310
L2
304
306

400
402
404
406
410
412
408

400
404
406
410
408

500
506
532
500
D1
L2
L1

500
502
512
518
506
D2
LIGHT SOURCE

534
D1
D2

1. KIT

2. SNAP PENLIGHT INTO HANDLE AND TURN ON

3. APPLY LUBRICANT LIBERALLY TO SPECULUM

4. ADVANCE ENTIRE SPECULUM TO RESISTANCE

5. ADVANCE DILATOR TO DESIRED OPENING

6. APPLY VINEGAR (ACETIC ACID 5%) TO CERVIX

7. AFTER 45 SECONDS, OBSERVE CERVIX FOR ANY ACETOWHITE LESIONS

8. EXAMPLES OF PRE-CANCER/CANCER OF CERVIX

9. TURN CRYO BOTTLE UPSIDE DOWN AND SPRAY APPLICATOR FOR 10 SECONDS

10. APPLY TO WHITE LESIONS (IF PRESENT) FOR 45 SECONDS

11. PUSH DOWN ON RELEASE AND PULL DILATOR OUT

12. DISPOSE OF SPECULUM. SAVE PENLIGHT

VAGINAL SPECULUM AND CERVICAL SCREENING KIT

CROSS-REFERENCE TO RELATED APPLICATIONS

This application claims priority to the U.S. Provisional Application No. 63/280,438, filed on Nov. 17, 2021, entitled "VAGINAL SPECULUM AND CERVICAL SCREENING KIT". The contents of the above-noted application are incorporated herein by reference as if set forth in full and priority to this application is claimed to the full extent allowable under U.S. law and regulations.

FIELD OF THE INVENTION

The present invention relates to vaginal specula and, in particular, to a radially expanding speculum that improves visualization of the cervix and thereby enhances cervical analysis and procedures as well as associated structure for facilitating mounting of auxiliary equipment, e.g., for imaging or executing transvaginal medical procedures.

BACKGROUND

Vaginal specula are used to dilate the vagina and visualize the uterine cervix to screen and treat for cancerous and benign lesions of the cervix. Generally, existing vaginal specula are two-bladed including a stationary blade (relative to the speculum handle) and a pivoting blade. Some designs allow the pivot point to move linearly away from the stationary blades. Nonetheless, the moveable blade is substantially limited to moving away from and back towards the stationary blade in relation to one axis.

There are several drawbacks to existing speculum designs. The most important of these is the potential failure to fully visualize the cervix which could lead to failure to diagnose cervical cancer—a life threatening condition. In some women, with the two-bladed speculum, the vaginal walls collapse between the two-blades and obscure the view of the cervix. The current two-bladed design has relatively large blades that are difficult to introduce into the vagina of an apprehensive patient. In addition, the current speculum also does not take into account the variation in patient anatomy. The uterine cervix typically sits at a 90° angle to the vagina. The two-bladed speculum, as designed, opens asymmetrically. This may cause excessive dilation in certain parts of the vagina thus causing discomfort to the patient. Moreover, when closing and removing the two-bladed speculum, there are two "pinch points" along the length of the blade members, which can cause patient discomfort upon closing of the blades in preparation for withdrawal.

As noted above, the speculum may be used for diagnosis and treatment. Diagnosis or screening involves employing a speculum to visualize the patient's cervix and, in some cases, may further involve obtaining images of the cervix. Such images may be analyzed manually or by employing a digital analysis tool, e.g., accessed via a network. For example, a culposcope may be used for visualization as well as to obtain images for further analysis. Conventional culposcopes are large pieces of equipment supporting, in some cases, a binocular imaging system that can be positioned to view the patient's cervix through the central opening of a speculum. If a lesion or other condition of concern is identified, treatment may involve cryoablation, electrosurgical incision, or other transvaginal procedures via the central opening of the speculum.

Such diagnosis and treatment can be cumbersome to execute, sometimes requiring multiple skilled clinicians or otherwise involving some risk of misdiagnosis, mistreatment, or incomplete care. In particular, it is difficult for a single clinician to properly position the speculum while manipulating other equipment so that optimal visualization, imaging, or treatment can be executed. For example, positioning a colposcope may require a clinician to release the speculum. However, if pressure is released from the speculum, the speculum may be moved out of position or ejected from the patient, potentially requiring the use of a new speculum or at least requiring the speculum to be reinserted or repositioned, thus involving further discomfort for the patient and extending examination times. To avoid such outcomes, multiple clinicians may be involved but that may increase expense and be impractical for already underserved populations.

SUMMARY

The present invention is directed to a speculum that facilitates mounting of auxiliary equipment. In this manner, the clinician's hands are freed for use in additional procedures such as imaging or other medical procedures. In addition, a clinician may be able to utilize multiple pieces of equipment—such as a speculum, and electrosurgical instrument, and a smoke evacuation system—in a limited space, thereby potentially improving procedures and outcomes. A clinician can also readily implement cervical imaging processes and access diagnostic processing systems, including via remote processing platforms. In certain implementations, such functionality can be implemented using relatively low cost and readily available equipment and devices. The invention may also reduce the personnel required by a clinic to implement a range of diagnostic and treatment functions, thereby reducing costs and improving service for underserved populations.

In accordance with one aspect of the present invention, a method and apparatus ("utility") is provided for use in cervical imaging and diagnosis. The utility generally involves a speculum, an imaging system, and a data network. The speculum includes a distal portion, for positioning within a subject to dilate the subject to provide an enlarged opening to the subject's cervix in alignment with an axis of the speculum, and a proximal portion including a handle for gripping. The imaging system is employed for obtaining one or more images of the subject's cervix via the enlarged opening of the speculum. The data network is operatively associated with the imaging system for transmitting the images, via a data network, to a remote data terminal for analysis. The speculum further includes a mount for receiving structure of the imaging system in an imaging position in relation to the speculum for imaging the subject's cervix. The invention thus facilitates coordinated operation of a speculum and an imaging system thereby simplifying imaging and potentially improving results and reducing costs.

In one implementation, the imaging system includes a smart phone and the mount comprises an assembly for supporting the phone. For example, the support assembly may be disposed on a handle of the speculum. Preferably, the support assembly is movable in relation to the handle of the speculum to enable positioning of the phone for acquiring images as well as allowing the phone to be moved aside to accommodate other procedures. Alternatively, the imaging assembly may include an imaging detector and an optical element for use in transmitting imaging information from an optical interface to an imaging detector. In such cases, the mount may be adapted for supporting the detector or optical element.

In accordance with another aspect of the present invention, a utility is provided for facilitating mounting of auxiliary equipment for use with a speculum. The utility generally involves a speculum and a mounting system for mounting a medical device. The speculum includes a petal assembly, for positioning within an introitus of a subject to dilate the subject so as to provide an enlarged opening to the subject's cervix, and a dilator, separate from the petal assembly, for dilating and contracting the petal assembly. The mounting system is adapted for mounting the medical device on the dilator. For example, the mounting system may be adapted for holding a smoke evacuation tube, an imaging element of an imaging system, or equipment for executing a transvaginal procedure via a central opening of the speculum.

It will be appreciated that, among other things, the invention encompasses a speculum, methods for making and using the speculum, cervical screening and treatment processes involving the speculum and associated processing systems.

BRIEF DESCRIPTION OF THE DRAWINGS

For a more complete understanding of the present invention, and further advantages thereof, reference is now made to the following detailed description taken in conjunction with the drawings in which:

FIGS. 5C-5D, are top views of the speculum of FIGS. 5A-5B in the closed and open configurations, respectively;

FIGS. 5D-5F are side views of distal end petal portions of the speculum of FIGS. 5A-5B in the closed and open configurations, respectively;

DETAILED DESCRIPTION

In the following description, the invention is set forth with respect certain specific embodiments of vaginal specula and associated structure and equipment, as well as related functionality and processing. While these embodiments illustrate the principles of the present invention, it is anticipated that further embodiments of the invention are possible and will be apparent to those skilled in the art upon consideration of the present disclosure. Accordingly, the invention is not limited to the embodiments as set forth herein.

In the following description, various embodiments of the inventive speculum are first described. Thereafter, certain structure and functionality are described for facilitating mounting of auxiliary equipment on the inventive speculum, for example, for imaging and other medical procedures.

Speculum Embodiments

Figures 1A, 1B:
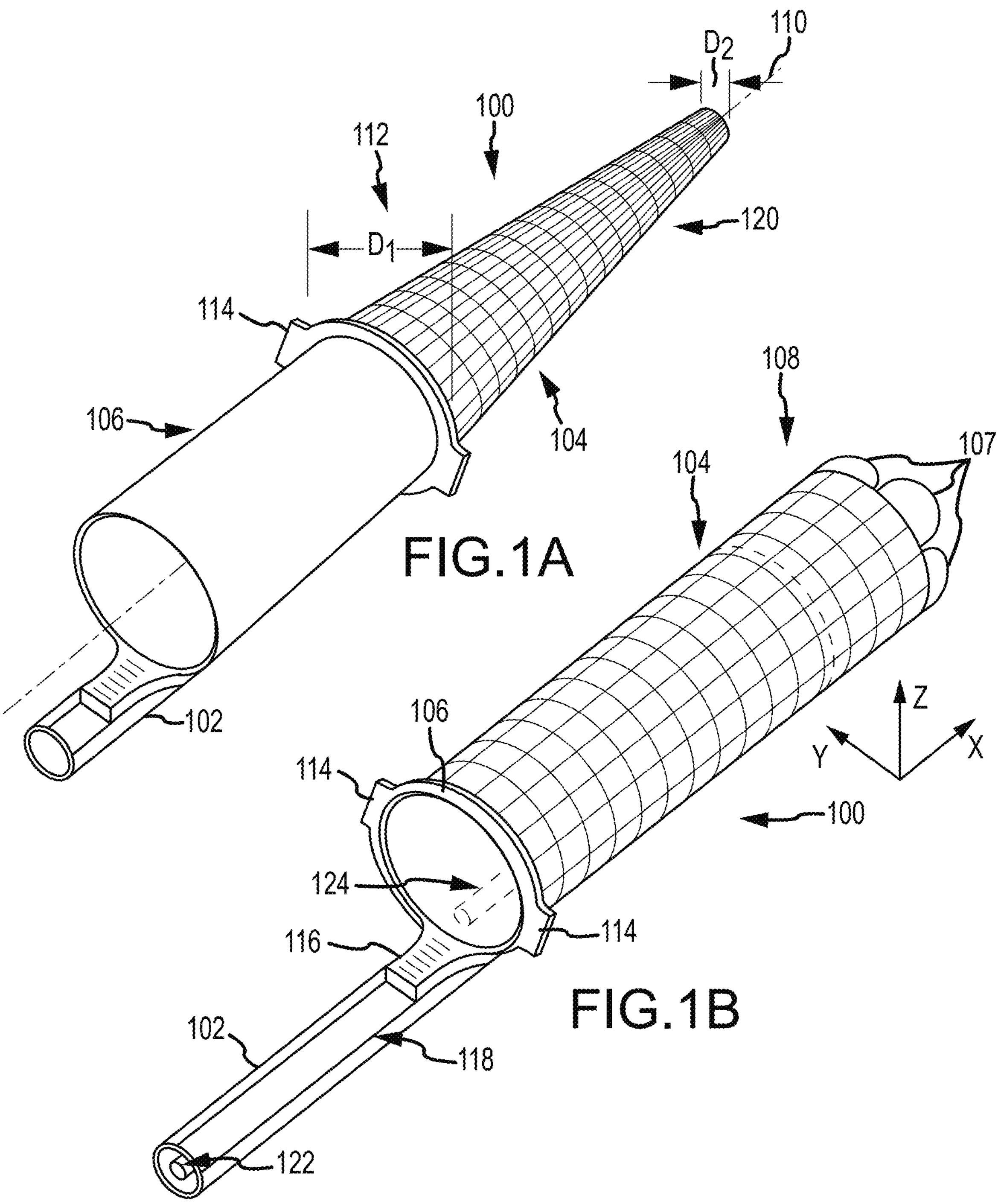
FIGS. 1A and 1B show perspective views of a vaginal speculum, constructed in accordance with the present invention, in a contracted (closed) and an expanded (open) configuration, respectively.

FIGS. 1A and B illustrate perspective views of a speculum 100 in accordance with the present invention. Specifically, FIG. 1A illustrates the speculum 100 in contracted or closed configuration and FIG. 1B illustrates the speculum 100 in a dilated or open configuration. The speculum 100 includes a handle 102 for gripping by a physician or other user, a petal assembly 104 for dilating and retaining the vaginal walls of the patient so as to facilitate visual inspection of the uterine walls and cervix as well as associated medical procedures, and a dilator 106 for use in introducing the petal assembly 104 into the patient and for forcing the petal assembly 104 to the expanded configuration as shown in FIG. 1B. Withdrawing the dilator 106 from the petal assembly 104 allows the petal assembly 104 to return to the contracted configuration as shown in FIG. 1A.

The illustrated petal assembly 104 includes a number of petals 107. As will described in more detail below, at the distal end 108 of the petal assembly 104, remote from the handle 102, the petals 107 can spread apart from one another so as to define the dilated configuration and can come back together in order to define the contracted configuration. The petal assembly 104 preferably includes at least three petals 107 to allow expansion with respect to at least two axes or two dimensions, e.g., the Y and Z dimensions as shown in FIGS. 1A and 1B where the X, Y and Z axes are mutually orthogonal and the X axis is aligned with the longitudinal axis 110 of the petal assembly 104. The illustrated petal assembly 104 includes four petals 107 each of which extends about approximately one quarter or 90° of the periphery of the petal assembly 104 at the distal end 108 in the contracted configuration. The petals 107 may alternatively overlap or remain somewhat separated (e.g., to avoid pinching) in the contracted configuration.

The petal assembly 104 has a generally hollow, truncated conical or bullet-shaped configuration. In the contracted configuration as shown in FIG. 1A, the petal assembly 104 has a diameter, $D_1$, at the proximal end 112, thereof, adjacent the handle 102 of about two inches and a diameter, $D_2$, at the distal end thereof about 0.75 inches. In the expanded configuration as shown in FIG. 1B, the diameter $D_2$ is, for example, about 1.5 inches. The illustrated petal assembly 104 further includes finger grips 114 that may be gripped by the physician or other user to facilitate insertion of the dilator 106 as will be described in more detail below. In the illustrated embodiment, as in the embodiments described below, the petal assembly 104 as well as the handle 102 and/or dilator 106 may be formed from a clear plastic resin, other plastic or metal. In this regard, plastic or resin materials allow for low cost construction as may be desired for single use disposable applications. The speculum 100 may be constructed from metal materials to allow for sterilization and reused if desired. In the illustrated embodiment, the petal assembly 104 is formed from a clear plastic resin.

For example, the body of the petal assembly 104 may be constructed by obtaining or molding the plastic resin in generally cylinderal or conical shape. The plastic resin can then be cut or slit from the distal end toward the proximate end 112 to define the petals 107. Alternatively, the petals 107 may be formed by appropriate molding. In any event, the petals 107 in the illustrated embodiment do not extend the full length of the petal assembly 104. Rather, the petals 107 come together at a location near the proximal end 112 to form a continuous cylinderal side wall. In this manner, the petals 107 flex outwardly to the expanded configuration when the dilator 106 is advanced into the hollow interior of petal assembly 104 from the proximal end 112. When the dilator is withdrawn from the hollow interior of the petal assembly 104, the petals 107 collapse to the contracted configuration, e.g., due to material memory of the clear plastic resin material or forces exerted on the exterior of the petal assembly 104 by the vaginal walls of the patient or by the user. Where metal materials are utilized, the petal assembly 104 can move between the expanded and the contracted configurations by flexing of the metal materials or by hinge mechanisms.

As noted above, the dilator 106 may be formed from plastic, metal or other materials. In the illustrated embodiment, the dilator is formed from a clear plastic resin material. The dilator 106 may have a generally cylindrical or conical configuration and is dimensioned to be received within the hollow interior of the petal assembly 104 at the proximal end 112 thereof. That is, the outside diameter of the dilator 106 (at least the proximal end thereof) is slightly smaller than the inside diameter of the petal assembly 104 at the proximal end 112. For example, the outside diameter of the dilator 106 at its proximal end thereof may be between about 1.5 and 2 inches.

The illustrated dilator 106 has a thumb grip 116 extending from the rear surface thereof. The thumb grip 116 can be gripped by the user to advance the dilator 106 into petal assembly 104 and to withdraw the dilator 106 from the petal assembly 104. In the illustrated embodiment, the dilator 106 includes a rib (not shown) extending from the bottom of the dilator 106. This rib and/or the bottom of thump grip 116 runs in a longitudinal dilator track 118 formed in an outer surface of the handle 102 so as to guide the longitudinal movement of the dilator 106. The thumb grip 116 may be ergonomically shaped and textured so as to facilitate operation by a physician or other user. In the case of a conical dilator 106 can be inserted, distal end first, into the petal assembly 104 to facilitate introduction of the petal assembly 104 into the introitus. The dilator can then be flipped and reinserted into the petal assembly 104 proximal (fat) end first to expand the petal assembly 104 to the extent desired. In the case of a cylindrical dilator 106, the dilator 106 would be advanced into the petal assembly 104 only after the petal assembly 104 is positioned within the introitus. In such cases, the petal assembly 104 may be bullet-shaped to better resist petal separation during introduction. In this regard, a cylindrical dilator 106 may facilitate better visualization as it provides a wide aperture across its entire length. The dilator 106 may be advanced linearly (and may thereafter maintain its position by friction or a ratchet mechanism) or may be threaded so as to advance into the petal assembly 104 via a rotary, screw-like motion.

The illustrated speculum 100 also includes a latex sleeve 120 to protect against penetration of the vaginal walls between the petals and potential pinching. As can be seen in FIG. 1B, the petals 107 are separated from one another by spaces in the expanded configuration. As the petals 107 collapse to the contracted configuration, the edges of the petals come together creating a risk that of tissue of a patient will be captured therebetween and pinched. This risk can be reduced by use of the optional latex sleeve 120. The latex sleeve 120 can be placed over the petal assembly 104 at one end thereof and unrolled like a condom to extend around substantially the entire external surface of the petal assembly 104. In this manner, the latex sleeve 120 guards against collapsing of the patient's uterine wall tissue into the spaces between the petals 107.

The handle 102 of the illustrated embodiment has a generally cylindrical configuration. If desired, the exterior surface of the handle 102 may be formed for improved ergonomics. The illustrated handle 102 has a hollow interior cylinder receptacle 122 dimensioned to receive a light source. The light source can be activated by the user to transmit light through the handle 102 and through the petal assembly 104 so as to illuminate a procedure site such as the patient's uterine walls and/or cervix. In the illustrated embodiment a light pipe 124 is formed in a portion of the petal assembly 104 to guide light to and concrete light on the procedure site. Conventional vaginal specula typically require an expensive custom light source. Though such light sources can be provided in connection with illustrated speculum 100, the illustrated speculum 100 can also be designed to receive an inexpensive pen light within the cylinder receptacle 122. The cylinder receptacle 122 may be formed so that the pen light is turned on, e.g., by depressing a button on the pen light, when the pen light is inserted into the cylinder receptacle 122. Alternatively, the pen light may have an on/off button exposed at a rear end thereof that can be accessed by the user after the pen light is inserted into cylinder receptacle 122.

Figures 2A, 2B:
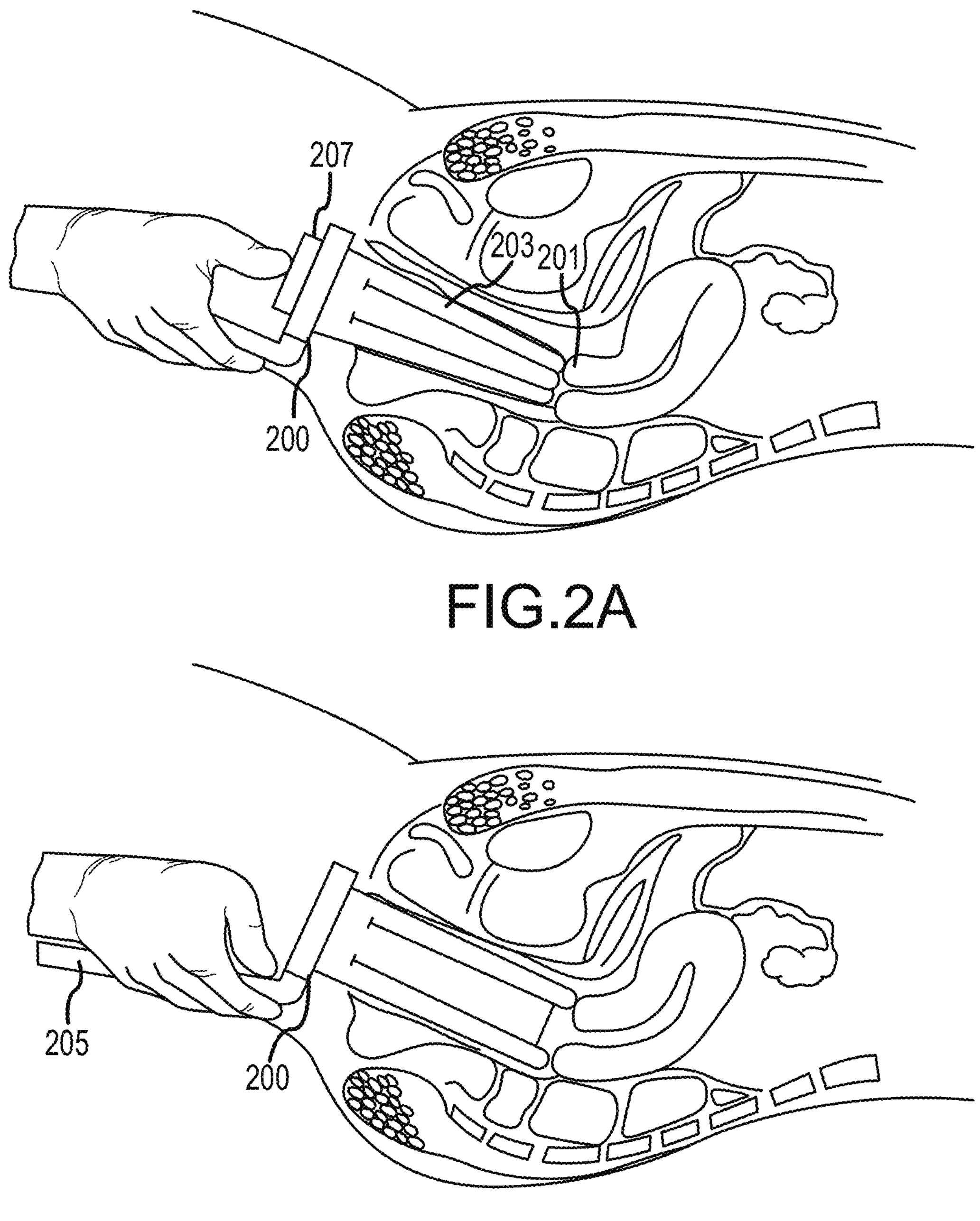
FIGS. 2A and 2B illustrate a vaginal speculum in accordance with the present invention in contracted and expanded configurations, respectively, where the speculum in shown inserted into the introitus of a patient and certain physiology of the patient is depicted for purposes of illustration.

FIGS. 2A and 2B illustrate a speculum 200, generally similar in construction to the speculum 100 of FIGS. 1A and 1B but with a slightly different configuration, for use on a patient. Specifically, in use, the speculum 200 can be introduced into the introitus of the patient in a contracted configuration as shown in FIG. 2A. As shown, the speculum 200 is advanced into the patient until the distal end of the speculum 200 is adjacent to the patient's cervix 201. It will be appreciated that the speculum 200 is dimensioned appropriately in this regard. For example, the petal assembly 203 may have a length of about 6.5 inches and the handle 205 may have a length of about 3.5 inches for an overall speculum length of about 10 inches. Such dimensions are believed to accommodate a substantial range of physiological variability among patients. Once the speculum 200 has been inserted to the full extent desired, the physician or other user can advance the dilator 207 into the proximal end of the petal assembly 203 so that the petals of the petal assembly are radially separated.

It will be appreciated, that, in the case of a four petal assembly as described in connection with FIGS. 1A and 1B, two of the petals may separate along a front to back axis with respect to the patient and two of the petals may separate along a side to side axis with respect to the patient. This creates an unobstructed view. The petals may be formed to separate along other axes if desired. The user can then insert or otherwise activate a light source at the speculum handle 205 to illuminate the uterine walls and cervix of the patient. The physician or other user can then visually inspect the uterine walls and cervix of the patient by looking through the hollow interior of the dilator 207 and petal assembly 203 to obtain a clear view of the procedure site. When the inspection or any other desired procedure (e.g., obtaining an analysis sample by introducing an instrument through the hollow interior of the speculum) is complete, the dilator 207 is withdrawn from the petal assembly 203 allowing the petal assembly 203 to collapse to the contracted configuration. The speculum 200 can then be withdrawn from the patient's introitus and disposed of and or sterilized as appropriate.

FIGS. 3A-3G illustrates a speculum 300 constructed in accordance with alternative embodiment of the present invention. The speculum 300 generally includes a petal assembly 302 a handle 304 including a receptacle 306 for holding a light source 308 and a ratchet assembly 310 for use in expanding the petal assembly 302. The ratchet assembly 310 is operated using a thumb lever 312.

Figure 3A:
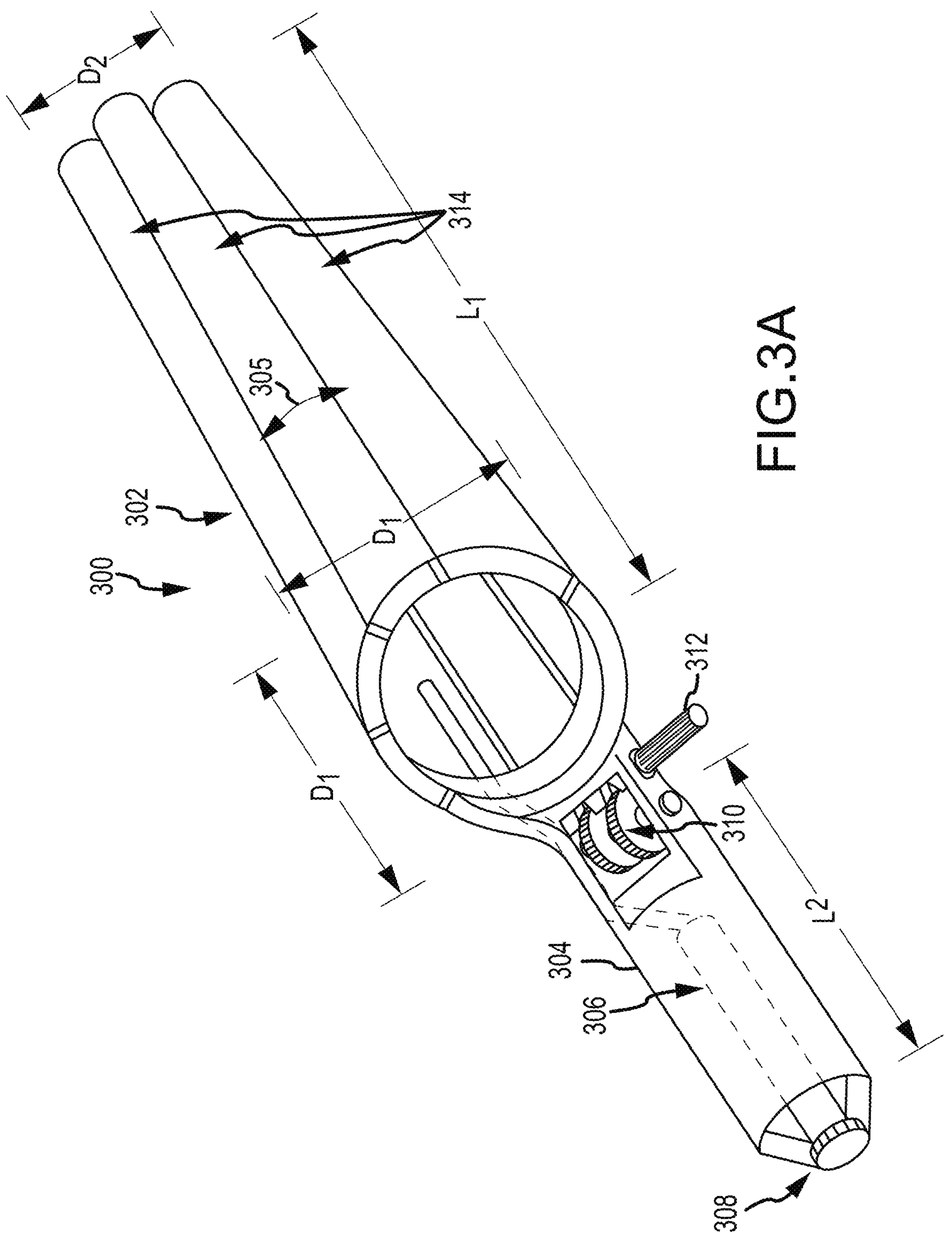
FIGS. 3A and 3B are perspective views of a vaginal speculum, in accordance with an alternate embodiment of the present invention, in expanded and contracted configurations, respectively.
Figure 3B:
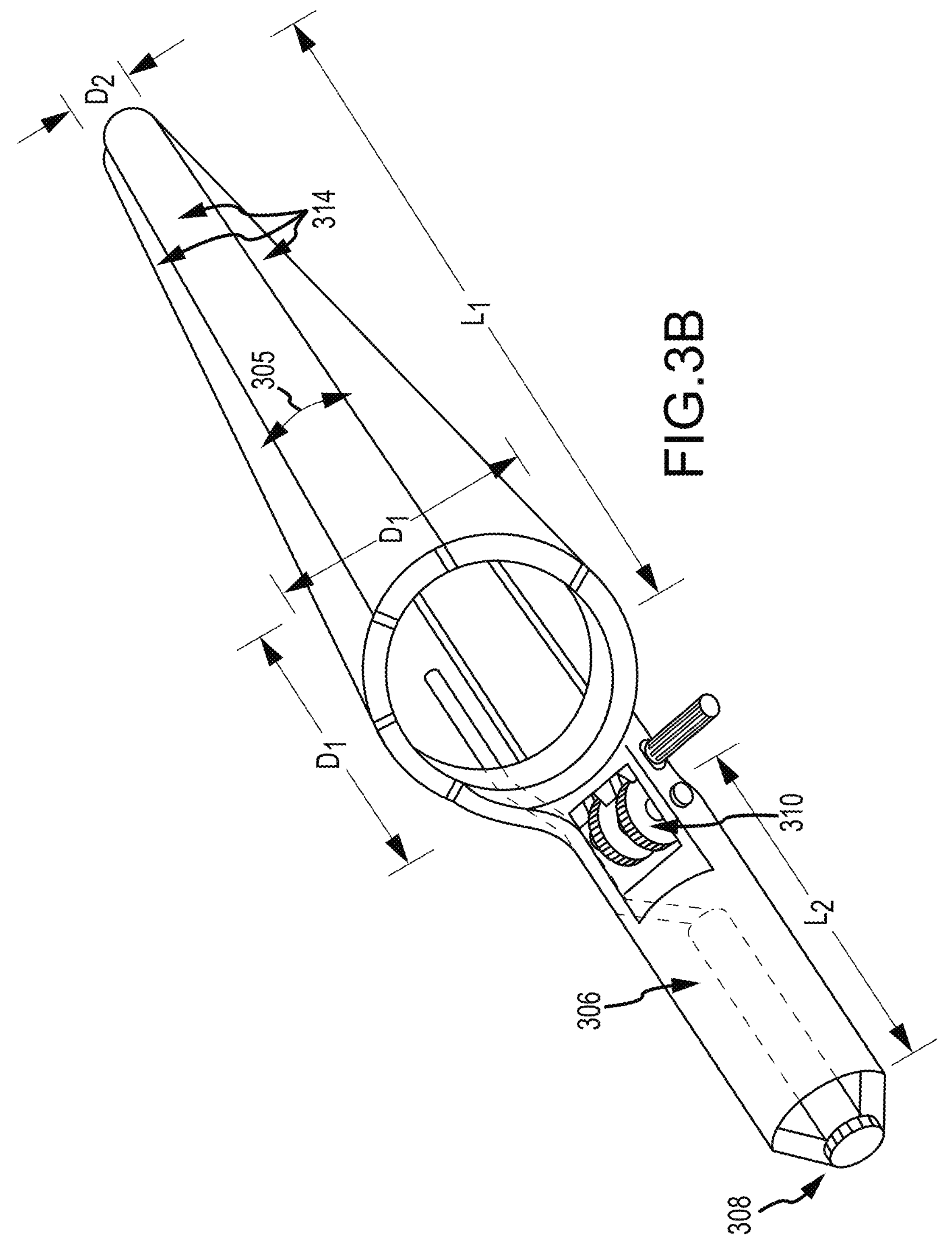
Figures 3C, 3D:
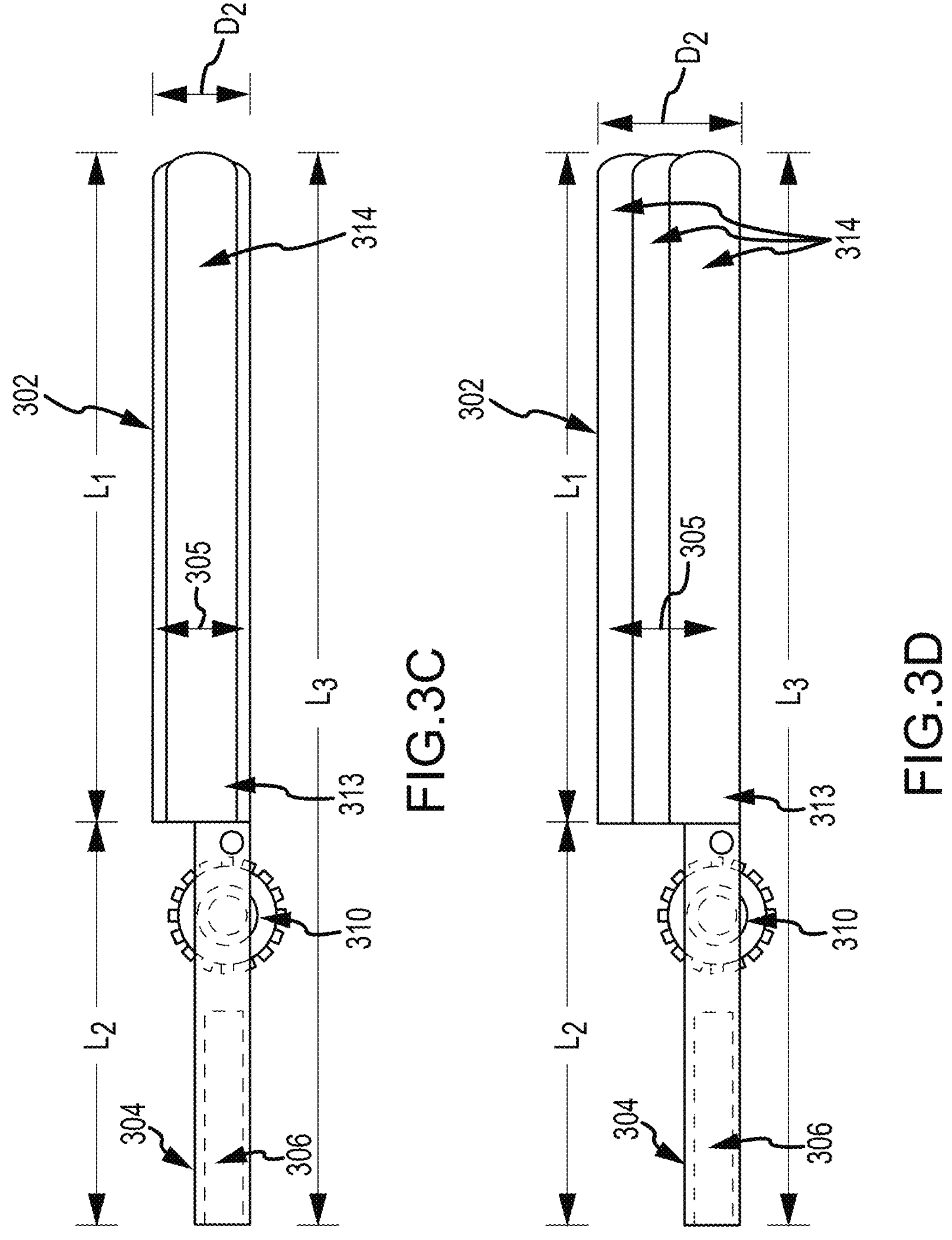
FIG. 3C is a side view of the speculum of FIGS. 3A-3B in the contracted configuration.
FIG. 3D is a side view of the speculum of FIG. 3A in the expanded configuration.

The speculum 300 of FIGS. 3A-3E shares many characteristics with the speculum of FIGS. 1A and 1B. For example, the speculum 300 is used by inserting the petal assembly 302 into the patient's introitus with the speculum 300 in a contracted configuration (as shown in FIGS. 3B and 3C). The speculum 300 is then expanded to the dilated configuration (as shown in FIGS. 3A and 3D). The light source 308 can then be activated to illuminate patient's vaginal walls and cervix which can be inspected visually by looking through the hollow petal assembly 302. Moreover, like the embodiment of FIGS. 1A and 1B, the speculum 300 expands radially with respect to multiple axes for improved viewing without interference due to collapsing vaginal walls.

However, the speculum 300 has some differences in relation to the embodiment of FIGS. 1A and 1B. In particular, whereas the petals in FIGS. 1A and 1B are separated by spaces at least in the expanded configuration, the petals 314 of the speculum 300 overlap as can best be seen in FIGS. 3E and 3G. When the petal assembly 302 is expanded or contracted, the petals slide circumferentially over one another (as generally indicated by arrows 305) in manner analogous to a collapsible colander. Accordingly, there are no spaces between the petals in either the expanded contracted configuration. This may further protect against collapsing of the vaginal walls and potential pinching.

Figures 3E, 3F, 3G:
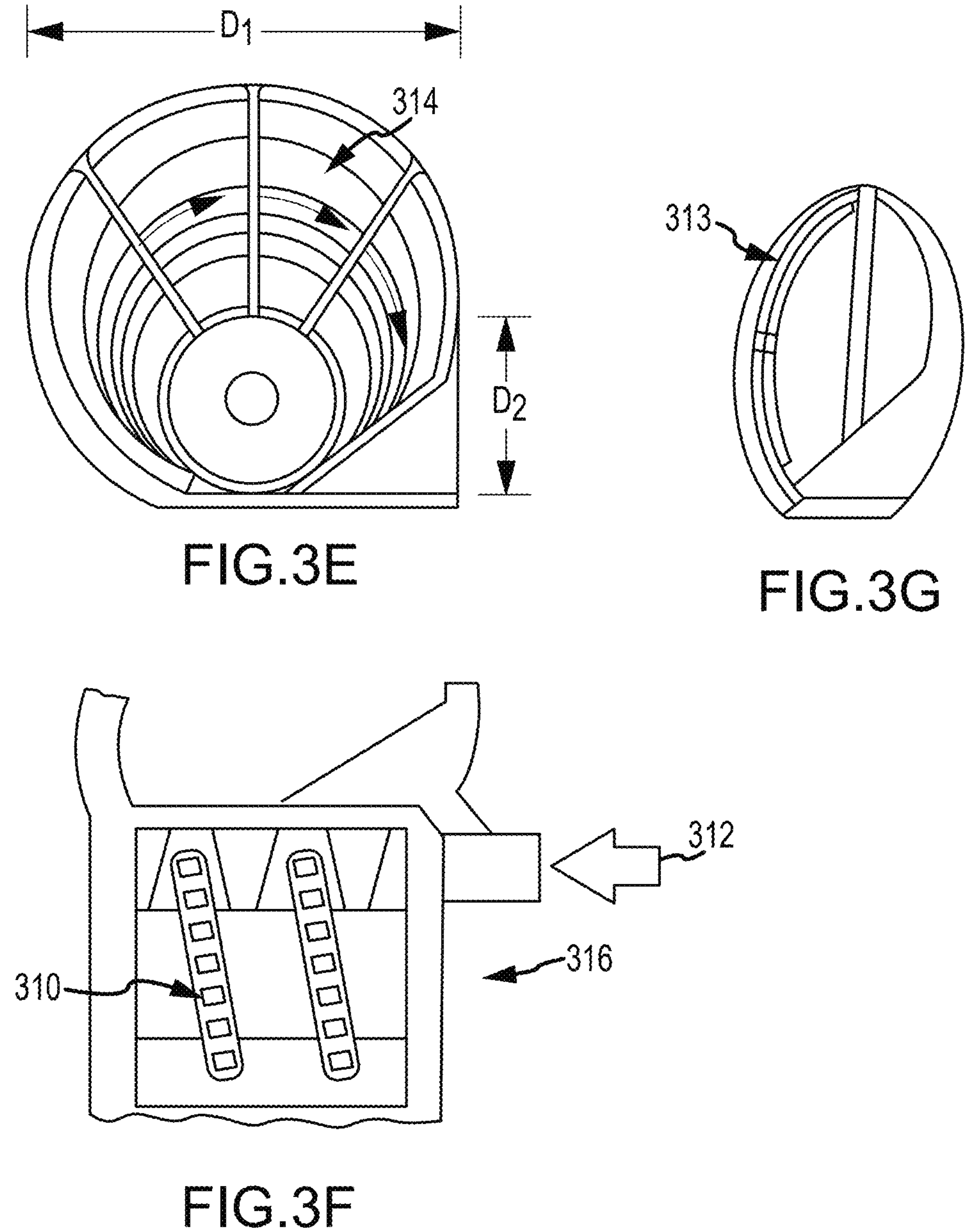
FIG. 3E is a end view of the dilation assembly of the speculum of FIGS. 3A-3B.
FIG. 3F is a expanded view of the worm gear ratchet mechanism of the speculum of FIGS. 3A and 3B.
FIG. 3G is a expanded view of the linkage for interconnecting the worm gear racket assembly to the dilation assembly of the speculum of FIGS. 3A and 3B.
Figure 4A:
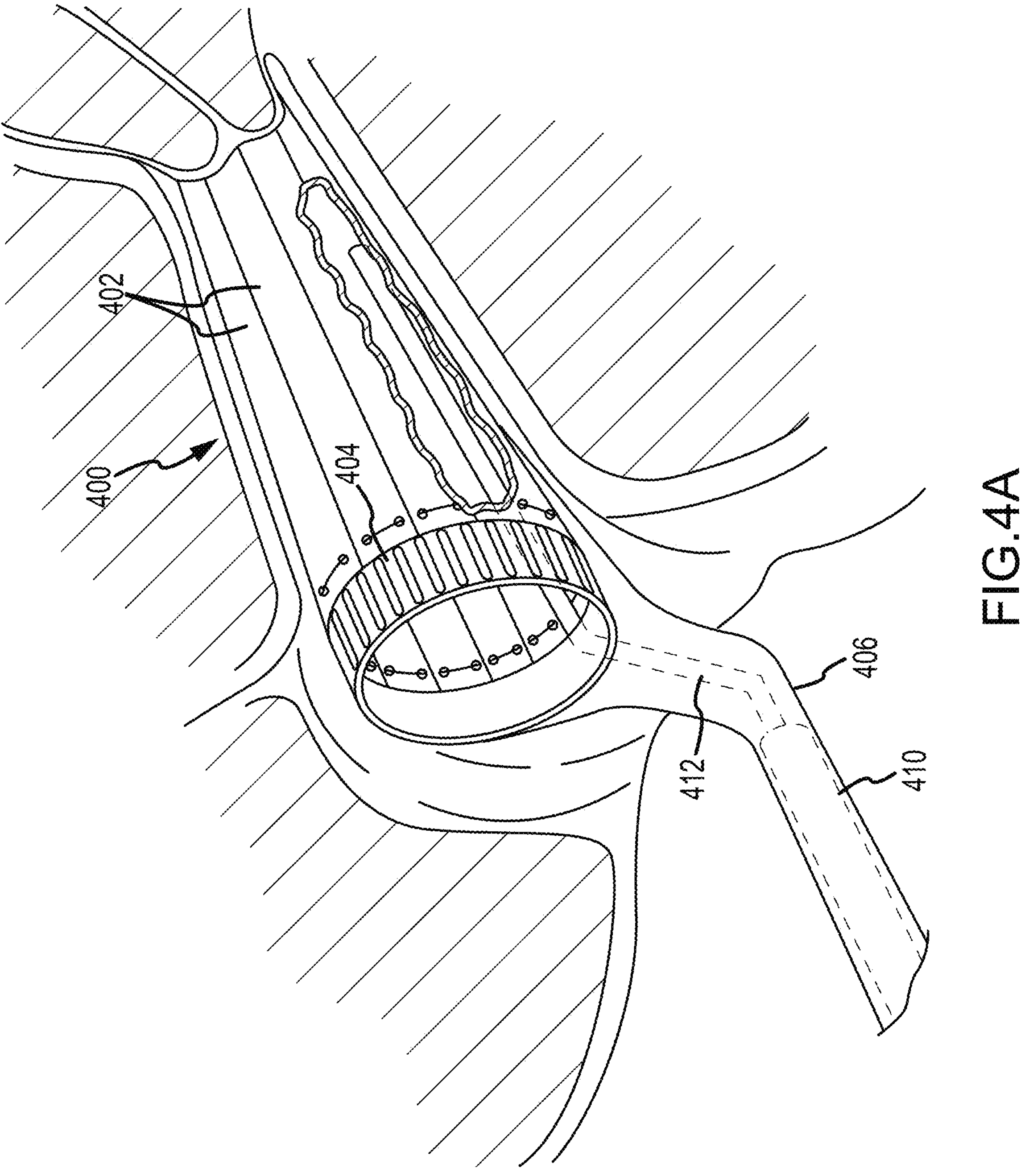
FIG. 4A shows a speculum, in accordance with a still further embodiment of the present invention, positioned for inspection of a patient's cervix.
Figures 4B, 4C:
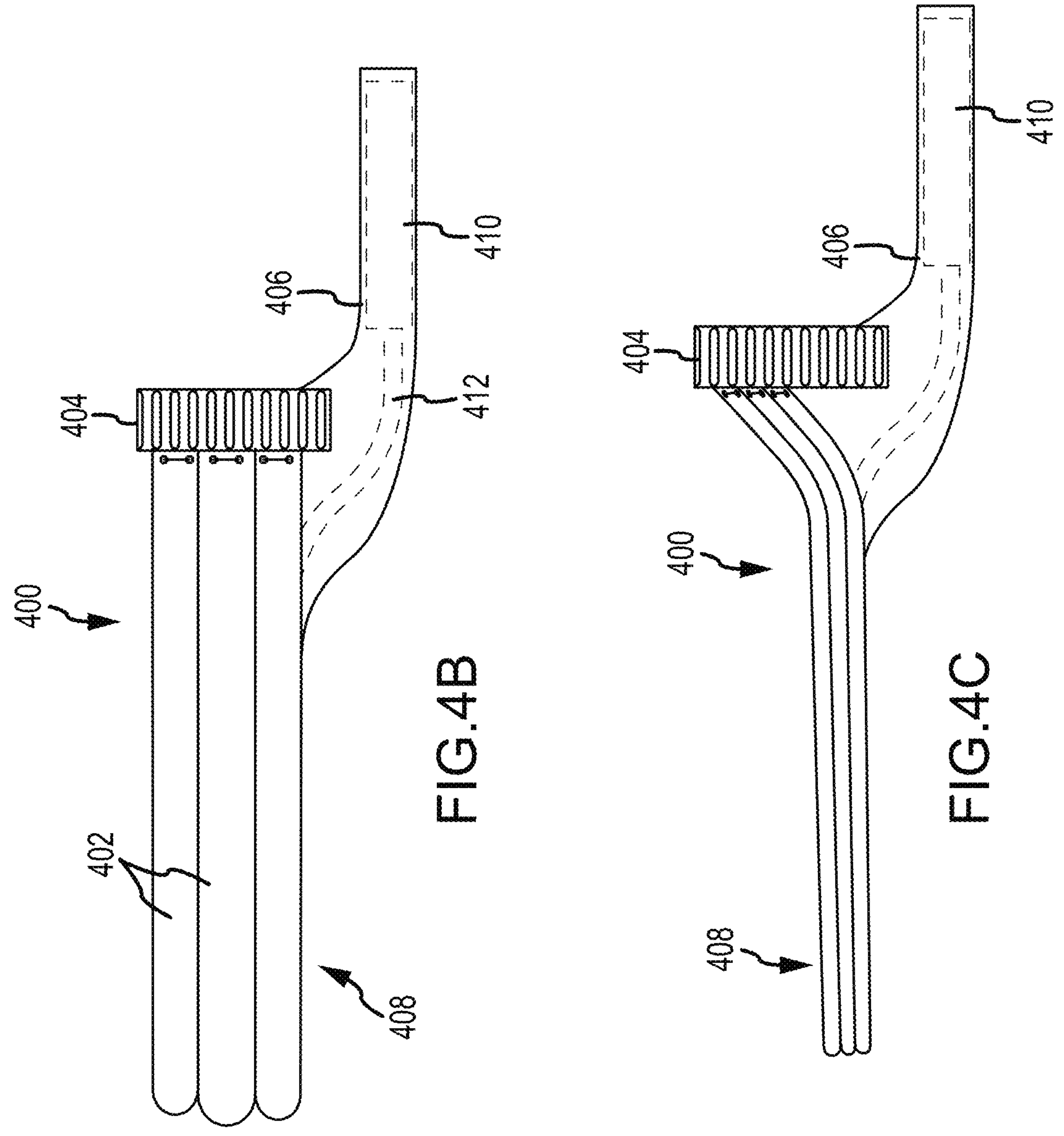
FIGS. 4B-4C are side views showing the speculum of FIG. 4A in the open and closed configurations respectively.
Figures 4D, 4E:
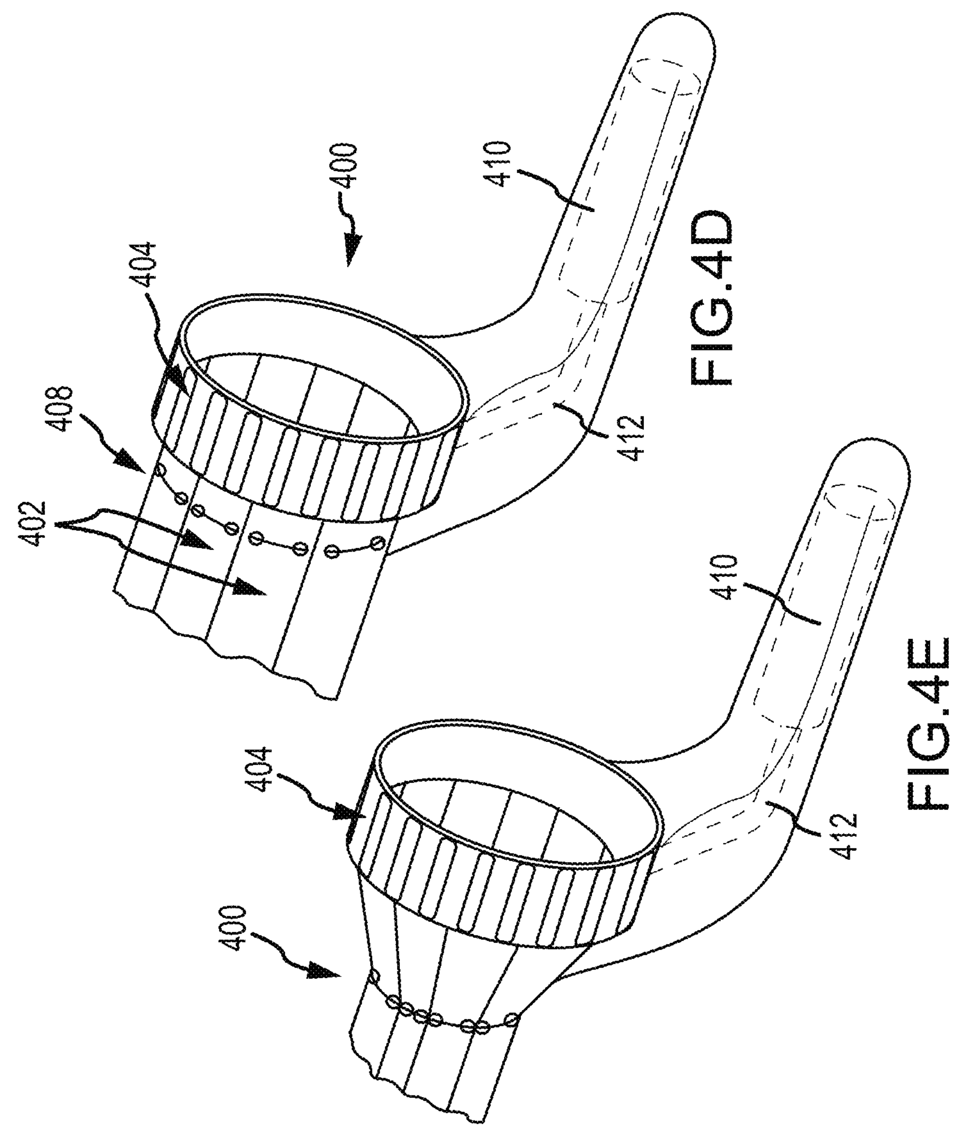
FIGS. 4D-4E show perspective views of a portion of the speculum of FIG. 4A in the open and closed configurations, respectively.

Another difference between the illustrated speculum 300 and that of FIGS. 1A and 1B is the mechanism for actuating expansion of the petal assembly 302. Specifically, the petal assembly 302 is expanded by operation of the thumb lever 312. The thumb lever 312 interfaces with a worm gear ratchet as shown in FIG. 3F such that depressing the thumb lever closes the speculum 300 to the contracted configuration and pulling outwardly on the thumb lever 312 causes the speculum 300 to be expanded to the dilated configuration. The thumb lever 312 causes the worm gear of ratchet assembly 316 to rotate. The worm gear ratchet assembly 316 is then connected to the proximal ends 313 of the petals 314 by appropriate linkage (as shown in FIGS. 3F and 3G) to expand and contract the petal assembly 302 as desired.

The illustrated speculum 300 is dimensioned to accommodate a range of patients including larger patients. For example, the diameter $D_1$, of the proximal end of the petal assembly 302 may be about 1.5 inches. The diameter, $D_2$, of the distal end of the petal assembly may be about 1.4 inches in the expanded configuration and about 0.7 inches in the contracted configuration. The petal assembly 302 has a length, $L_1$, of about 6.5 inches and the handle 304 has a length, $L_2$, of about 3.5 inches for an overall length, $L_3$, of about 10 inches for the speculum 300.

FIGS. 4A-4E illustrate a still further embodiment of a speculum 400 in accordance with the present invention. The speculum 400 includes a number of overlapping speculum petals 402 generally similar to the petals in the embodiment of the FIGS. 3A-3G. In this case, however, the petals are expanded and contracted directly by rotating retention ring 404 rather than using a ratchet assembly as described in connection with the embodiment of FIGS. 3A-3G. In addition, the handle 406 is offset vertically, by offset structure 407, from the expansion assembly 408 which may facilitate visual inspection through the expansion assembly 408. The handle 406 further includes a receptacle 410 for receiving a light source and a light pipe 412 for directing light from the source to the patient's cervix.

FIGS. 5A-5F illustrate a speculum 500 in accordance with a still further embodiment of the present invention. The speculum 500 is similar to the speculum 100 of FIGS. 1A-1B, with some additional features shown and minor differences in configuration. The speculum 500 generally includes: a generally conical petal assembly 502 including a number of petals 504; a generally cylindrical dilator 506 for expanding the petal assembly 502 and allowing it to contract; and a handle 508 including a receptacle 510 for receiving a light source 512. As discussed above, the speculum can be formed, for example, from clear plastic or metal as desired.

The illustrated petals 504 are formed in an overlapping, collapsible configuration. That is, adjacent petals 504 extend circumferentially over one another, and slide over one another as the petal assembly 502 is expanded and contracted. In this manner, gaps between the petals 504 are avoided, even in the expanded configuration, thus reducing the likelihood that tissue of the patient will be pinched due to operation of the speculum 500.

The speculum 500 further includes a ratchet mechanism 514 for advancing and withdrawing the dilator 506 into and out of the petal assembly 502. The ratchet mechanism 514 includes a ratcheted handle surface 516 that interfaces with a bottom of a thumb lever 518. The thumb lever 518 includes an advance surface 520 and a release surface 522. The physician or other user can press on the advance surface 520, as generally indicated by arrow 524, to move the thumb lever 518 forward. The thumb lever 518 presses against the dilator 506 so that it also moves forward thus expanding the petal assembly 502. The ratchet mechanism 514 is then effective to hold the speculum in the expanded configuration.

To release the ratchet mechanism 514 so that the dilator 506 can be withdrawn from the petal assembly 502 to close the petals 504, the user can press on the release surface 522 as generally indicated by arrow 526. This causes the rear edge of the thumb lever 578 to lift and disengages the ratchet mechanism 514. The user can then slide the thumb lever 518 rearwardly to withdraw the dilator 506 from the petal assembly 502.

As noted above, the handle 508 includes a receptacle 510 for receiving a light source 512. Although any appropriate light source can be used, the illustrated receptacle 510 can receive a low-cost pen light type of light source 512, thereby reducing costs and inconvenience in relation to some conventional systems. The light source 512 may have an on/off button at its rear end that can be easily accessed by the user during a procedure. Light from the light source is guided through the handle 508, and directed through the petal assembly 502 to the procedure site by a plastic light pipe 528. Optionally, a brightly colored tag 530 or strap may be attached to the light source 512 to assist in locating the light source and to remind the user not to accidentally dispose of the light source 512 when the speculum 500 is discarded after a single use.

The petals 504 of the illustrated speculum 500 overlap, as indicated by arrow 532, so that there are substantially no spaces between the petals 504 in the dilated configuration. In this regard, the petals 504 may move linearly (or arcuately with substantially no circumferential component) in a radial direction when expanding while maintaining their overlapped, stacked relationship at their proximal ends like flower petals, or the petals 504 may slide circumferentially over one another while expanding like an expandable colander.

Figure 5A:
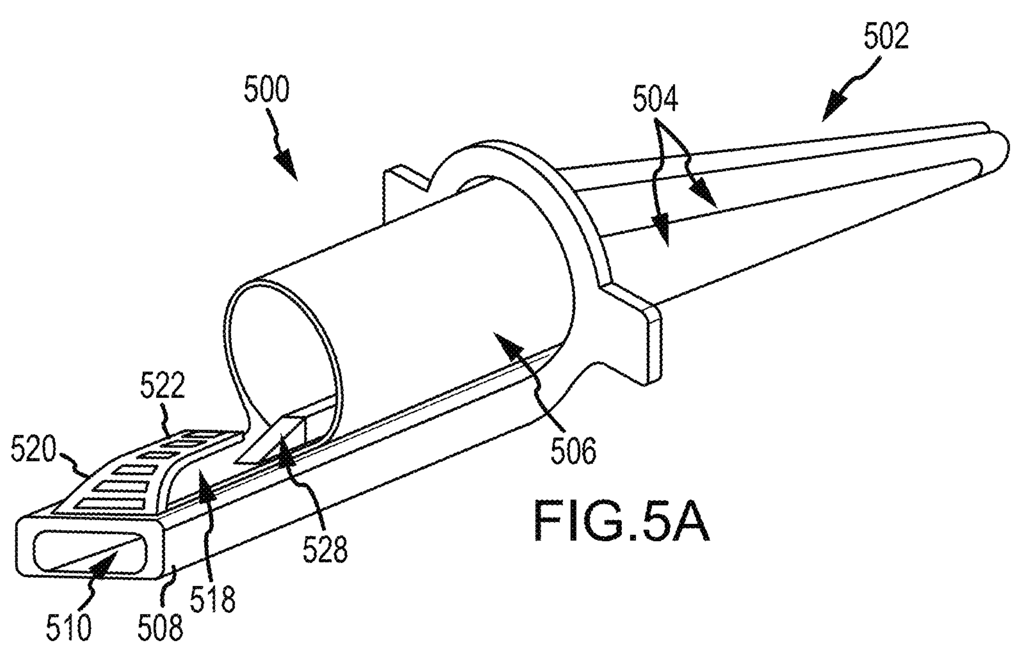
FIGS. 5A-5B, are perspective views of a speculum, in accordance with another embodiment of the present invention, in closed and open configurations, respectively.
Figure 5B:
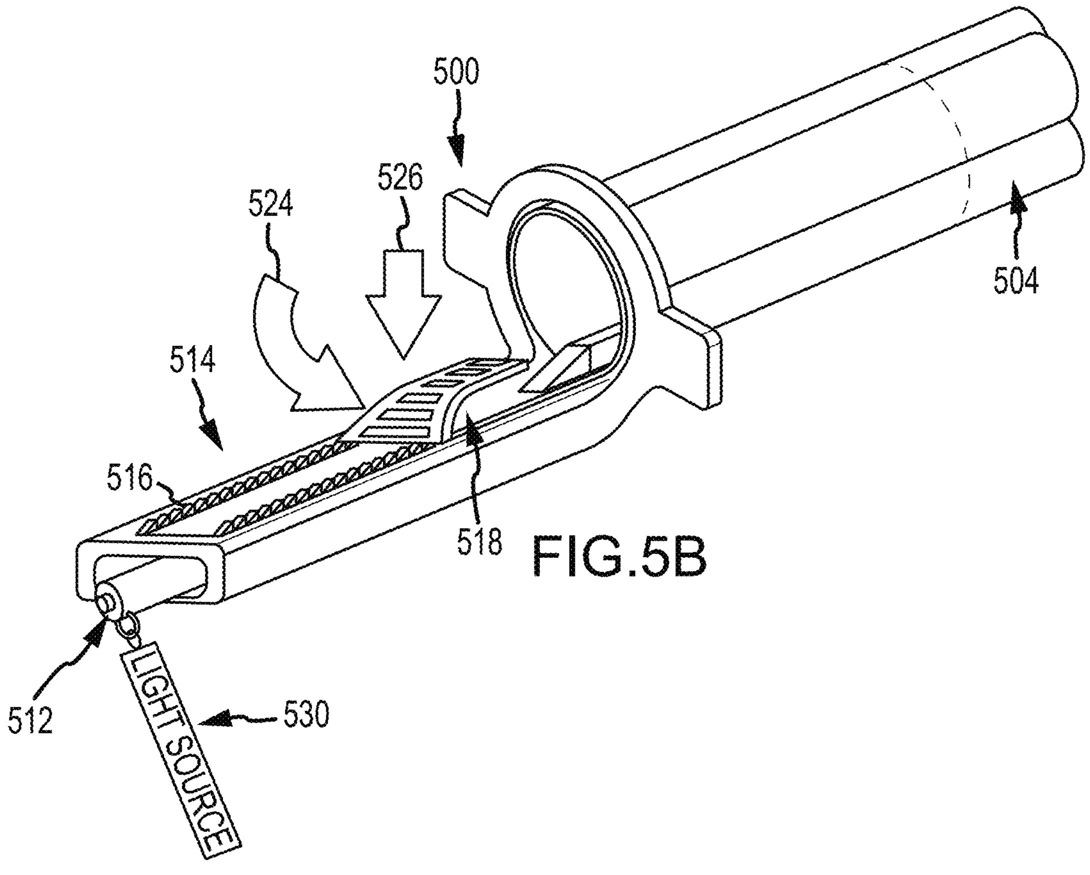
Figures 5C, 5D, 5E, 5F:
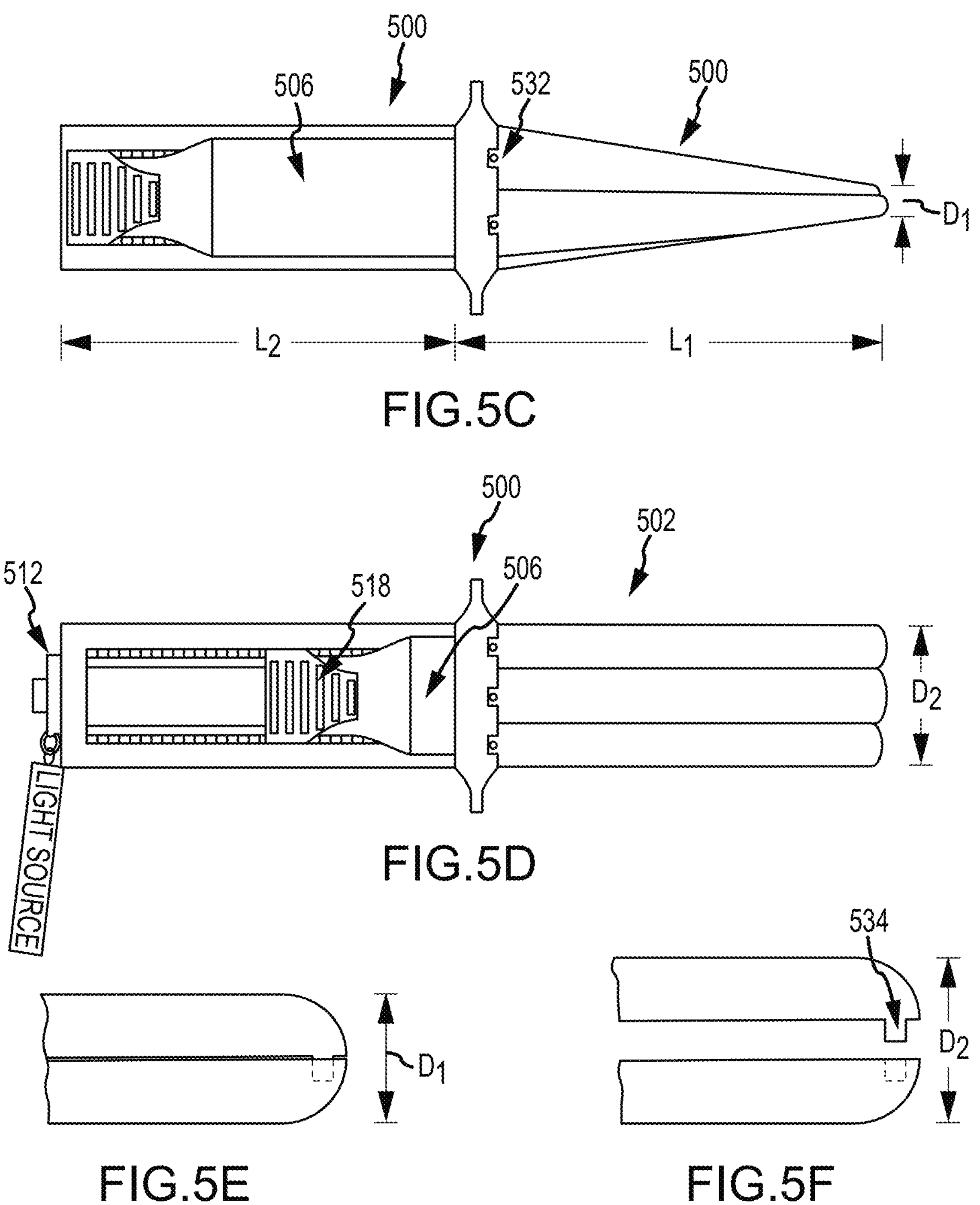

The speculum 500 is preferably dimensioned to accommodate a range of patients. For example, the petal assembly 502 may have a length $L_1$, of about 3.5 inches and the handle 508 may have a length, $L_2$, of about 3.5 inches for an overall speculum length of 7 inches. In the contracted configuration, the distal end of the petal assembly 502 has a diameter, $D_1$, of about 1.5 inches. The distal end of the petal assembly 502 preferably has a bullet-shaped configuration, as can be seen in FIG. 5E, that helps maintain the petal assembly 502 in the contracted configuration as the petal assembly 502 is introduced into the introitus. Optionally, one or more pegs 534 and mating receptacles may be provided at the distal end of the petal assembly 502 to further assist in maintaining the contracted configuration.

In the various embodiments disclosed above, the handles generally extend rearwardly in alignment with or at an acute angle to the longitudinal axis of the petal assembly in each case.

Another embodiment of a speculum 600 in accordance with the present invention is shown in FIGS. 6A-9B. The speculum 600 generally includes a speculum body 602 and a dilator 604. The speculum body 602, in turn, includes a petal assembly 606 and a handle 608.

Figure 6A:
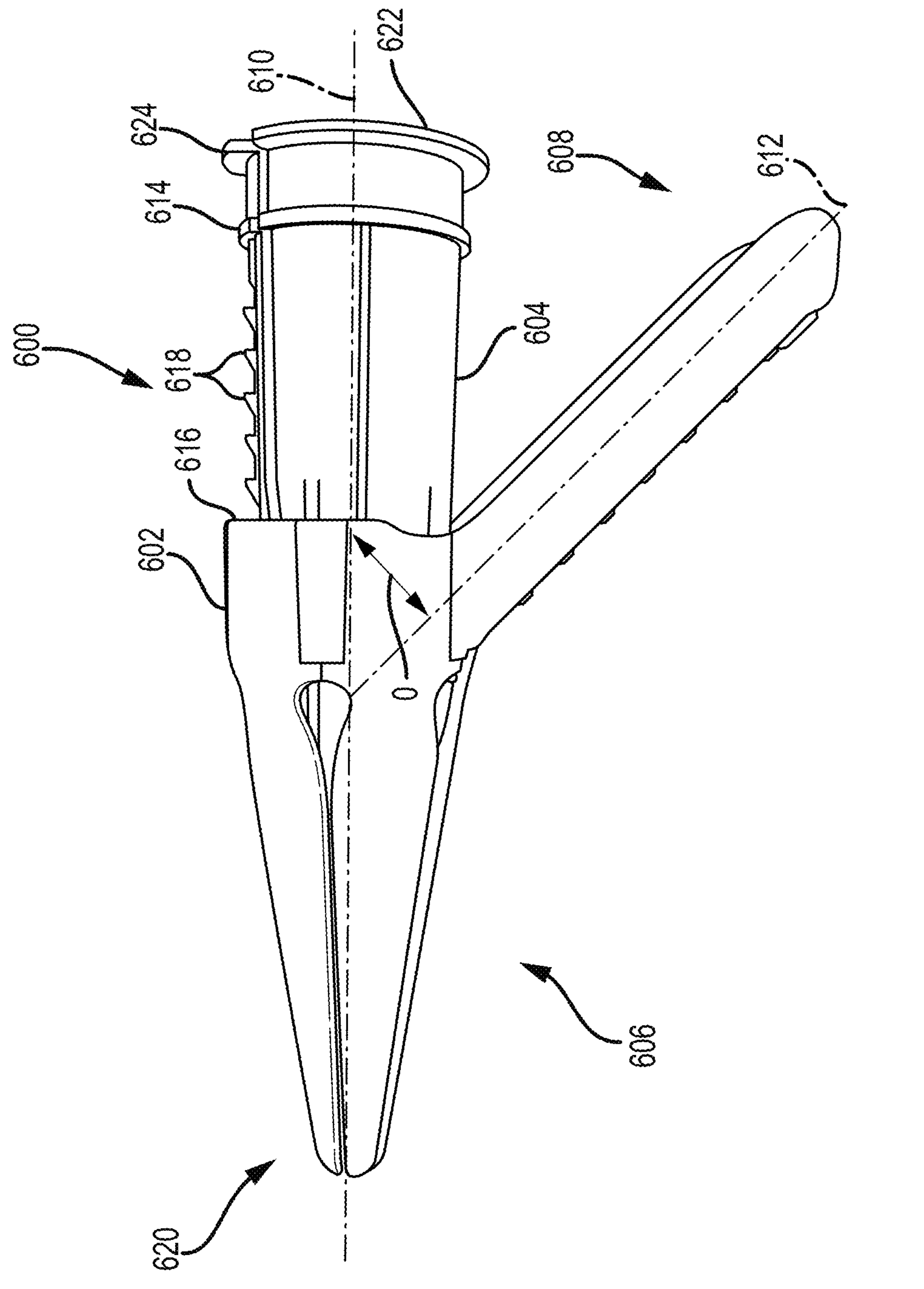
FIG. 6A is a side view of a speculum constructed in accordance with the present invention in a contracted configuration.
Figure 6B:
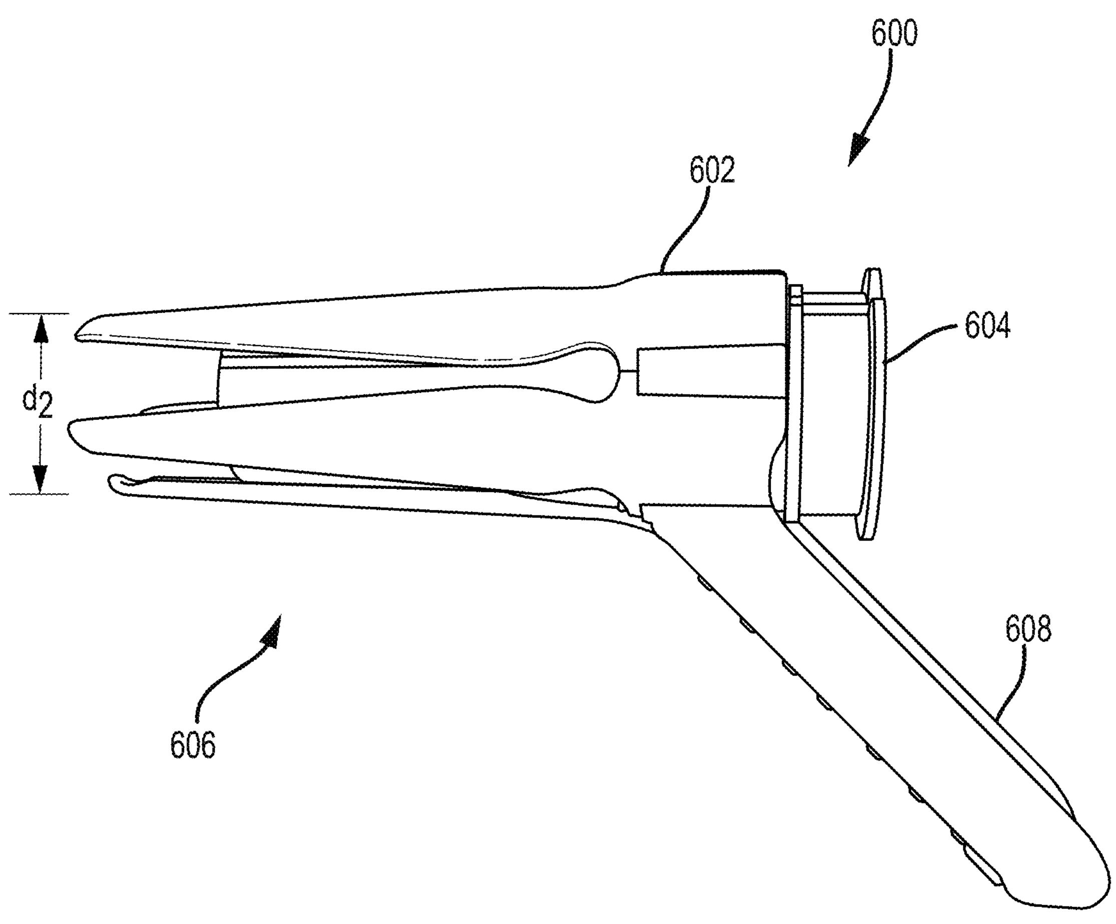
FIG. 6B is a side view of the speculum of FIG. 6A in a dilated configuration.

FIG. 6A shows the speculum 600 in a retracted configuration and FIG. 6B shows the speculum 600 in a dilated configuration. The speculum 600 is moved between the retracted and dilated configurations by advancing or withdrawing the dilator 604 relative to the speculum body 602 along the longitudinal axis 610 of the speculum 600. In the fully inserted position of the dilator 604, corresponding to the fully dilated configuration of the speculum 600, the collar 614 of dilator 604 buts against the rear surface 616 of the speculum body 602. The dilator 604 also includes ratchet teeth 618 that allow the dilator 604 to be positioned in various intermediate positions between the fully inserted and fully retracted positions. Such intermediate positions may be preferred depending, among other things, on the anatomy of the patient and the procedure being performed.

In operation, a user, who may be a physician, physician's assistant, clinic staff member or other person, can insert a light source 607 (FIG. 9B) into the handle 608, as will be described in more detail below, and turned the light source on. A sheath formed from latex or other suitable material may be applied around the forward end of the speculum 600, if desired, and a lubricant may be applied to the sheath or forward end. The user can then grip the speculum 600 using the handle 608 and advance the forward end 620 of the speculum 620 into the patient and advance the speculum 600 until the speculum 600 meets resistance. At that point, the user may press against the rear flange 622 of the dilator 604, for example, using the thumb of the same hand that grips the handle 608 or the user's other hand, and advances the dilator 604 in relation to the speculum body 602 to the desired position. Various procedures can then be performed as will be discussed in more detail below. At the conclusion of the procedure or procedures, the user can depress the ratchet release lever 624, for example, using the thumb of the same hand that grips the handle 608 or the user's other hand, allowing the dilator 604 to be withdrawn from the speculum body 602 to reach the fully retracted configuration. The speculum 600 can then be readily withdrawn from the patient.

The handle 608 of the illustrated speculum 600 is angled in relation to the petal assembly 606. More specifically, the handle 608 is oriented such that an angle, θ, that is less than 90°, is defined between the longitudinal axis 612 of the handle 608 in relation to the longitudinal axis 610 of the speculum 600 and petal assembly 606. Conventional specula have handles that are oriented perpendicular to the longitudinal axis of the speculum. This is customary and works well when the patient is reclined on an appropriate examination table. However, in many cases, including clinics in geographies where medical resources may be more limited, such an examination table may not be available. Moreover, the illustrated angled configuration facilitates convenient access to the dilator 604. At the same time, the angled configuration positions the user's hand on the handle 608 outside of a line of viewing and access to the patient generally corresponding to the longitudinal axis 610. It is noted that some of these considerations can alternatively be addressed by providing a handle that is generally aligned with the longitudinal axis of the speculum but is offset from the longitudinal axis of the speculum by depending structure extending between the handle and the speculum body as generally shown above.

In the illustrated embodiment, the angle, θ, is less than 75°. More preferably, the angle is between about 30°-75°. Most preferably, the angle is between about 40°-60°. In the illustrated embodiment, the angle is about 50°.

Figure 7A:
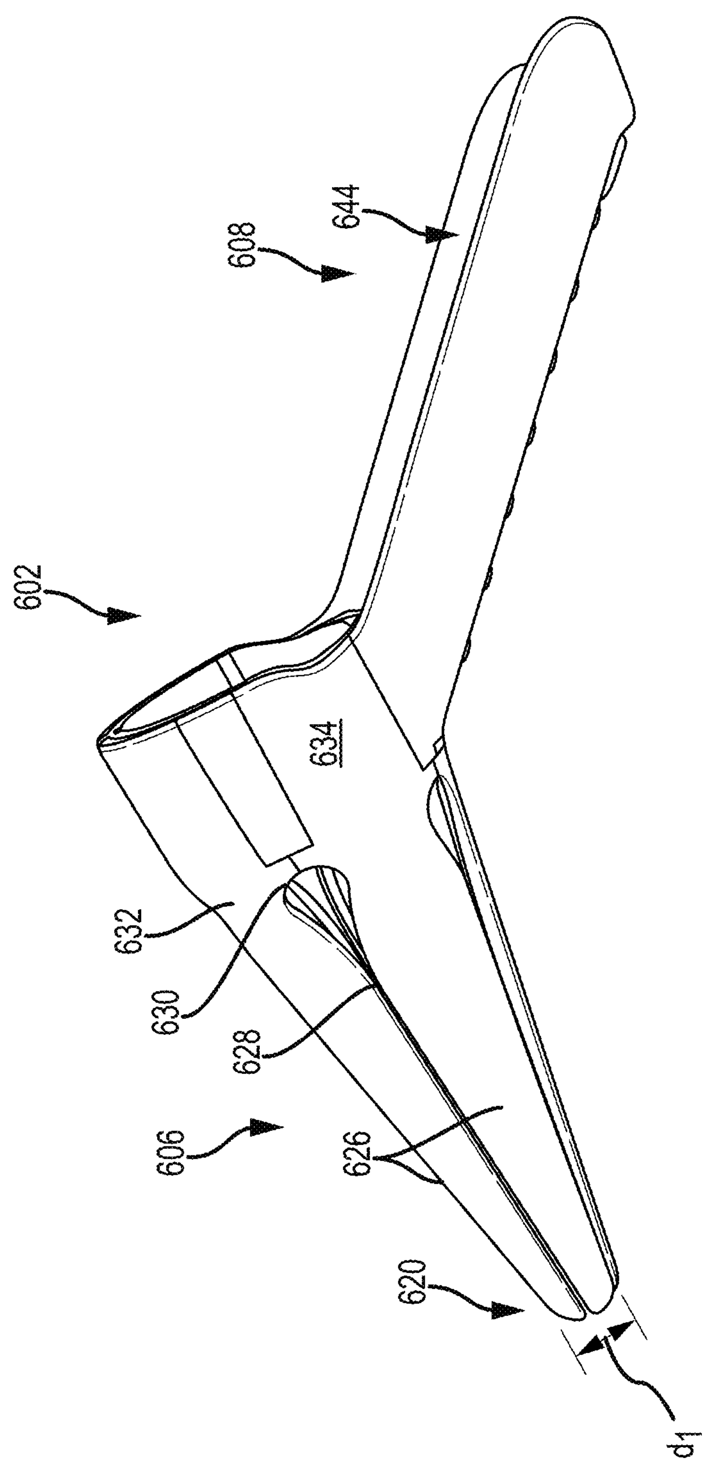
FIG. 7A is a perspective view of a speculum body of the speculum of FIG. 6A.
Figure 7B:
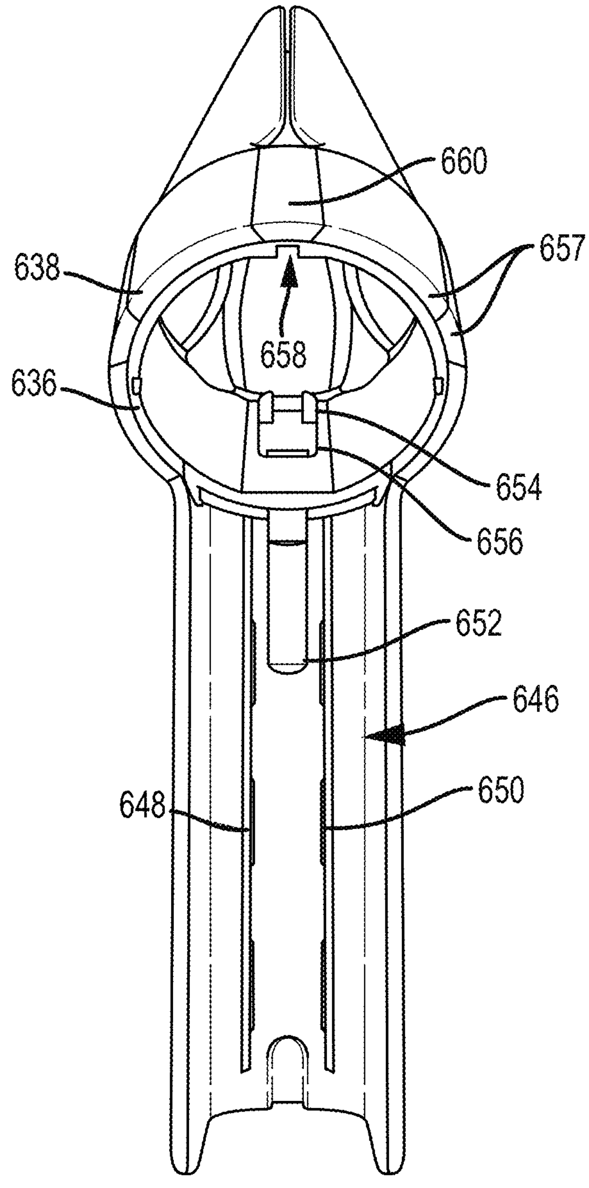
FIG. 7B is a rear perspective view of the speculum of FIG. 6A.
Figure 7C:
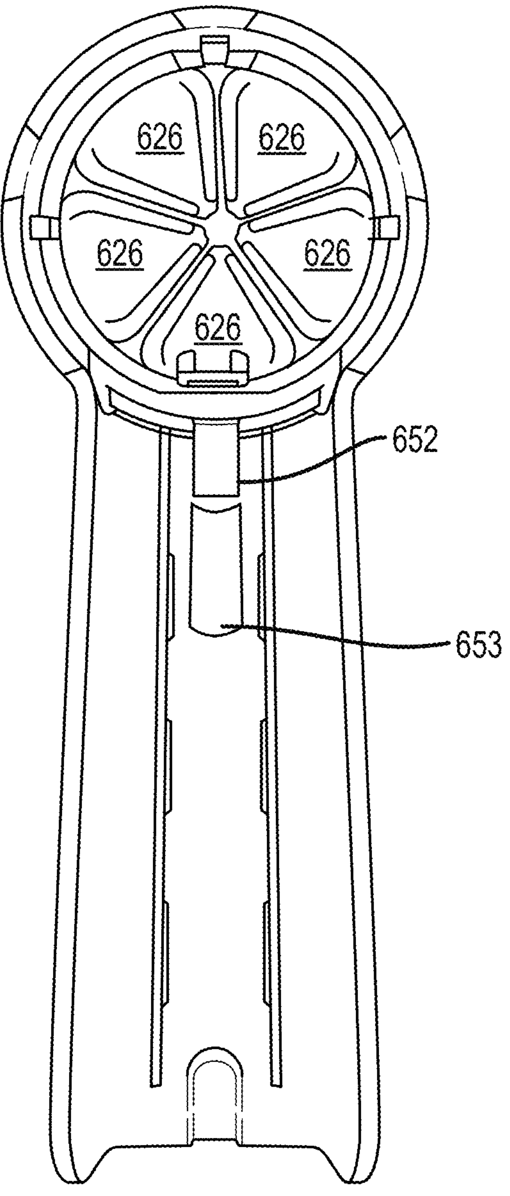
FIG. 7C is a rear view of the speculum of FIG. 6A.
Figure 7D:
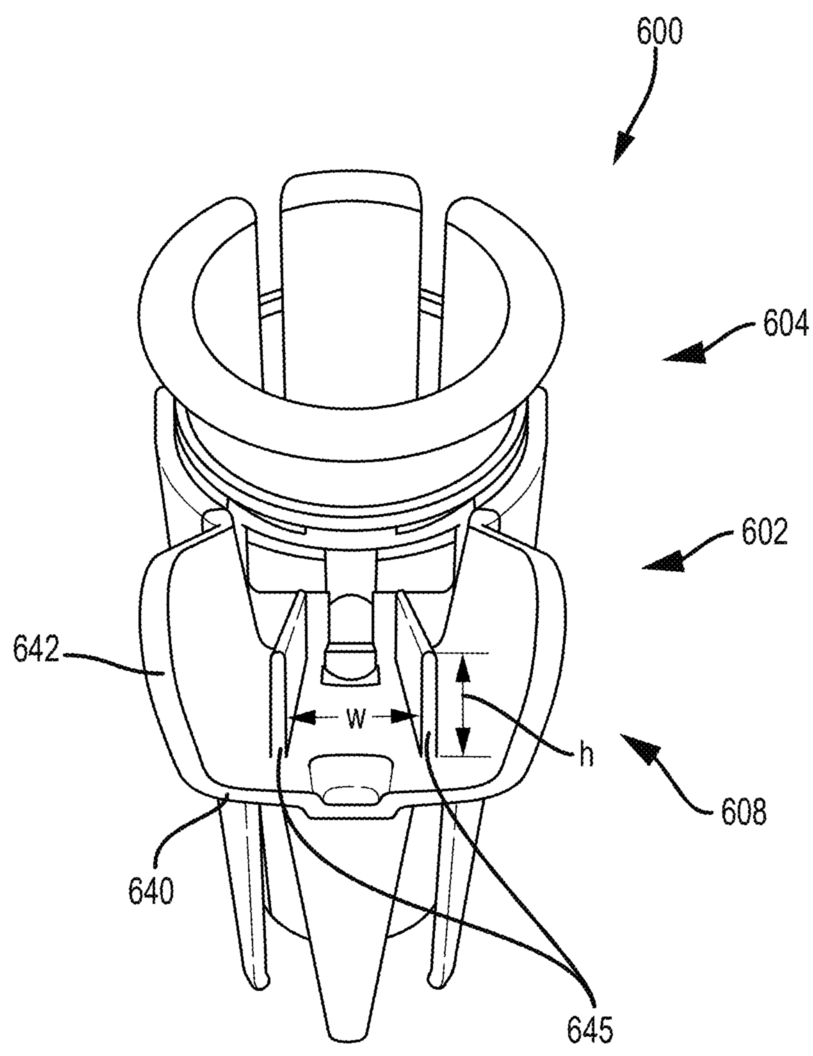
FIG. 7D is a perspective view of the speculum of FIG. 6A.
Figure 7E:
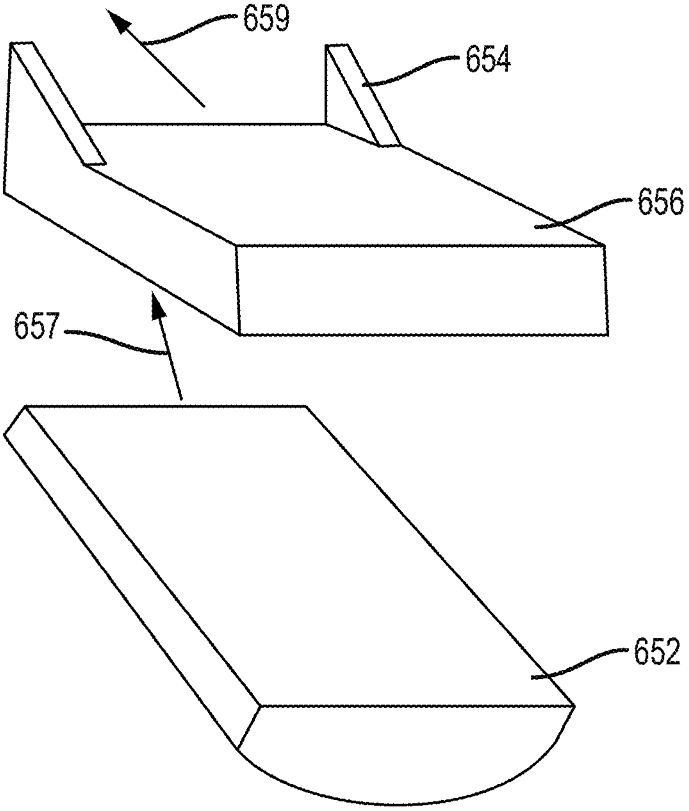
FIG. 7E is an exploded perspective view of certain components of the speculum of FIG. 6A.
Figure 7F:
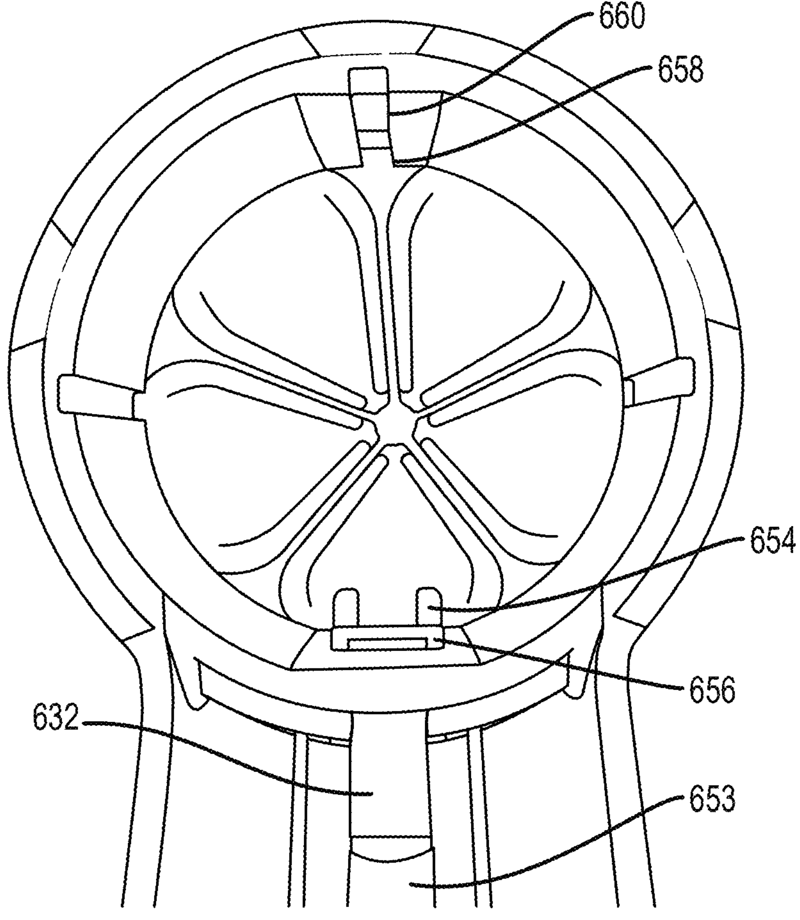
FIG. 7F is an enlarged perspective view of a portion of the speculum of FIG. 6A.

FIG. 7A-7E show various views of the speculum body 602. More specifically, FIGS. 7A-7C show the speculum body 602 alone in order to better illustrate certain features whereas FIG. 7D shows the full speculum 600 including the speculum body 602 and the dilator 604. FIG. 7E shows an expanded view of certain portions of the speculum body 602. As shown, the speculum body 602 includes the petal assembly 606 and the handle 608. The petal assembly 606 includes a number of petals 626. The number of petals 626 may vary, but the assembly 606 will generally include at least three petals 626 so as to allow for dilation relative to more than one axis for improved treatment site visualization and access. The assembly 606 may have many petals with the upper limit being determined by practical considerations such as ensuring that each petal 626 is sufficiently strong or stiff so as not to collapse under pressure from the vaginal walls. This will depend on a number of factors including materials, any stiffening structure formed in the petals 626, and the amount of support provided by the dilator 604 when inserted into the assembly 606. In the illustrated embodiment, five petals 626 are provided in the petal assembly 606.

At the forward end 620 of the assembly 606, each of the petals 626 is rounded and turned inwardly toward a centerline (generally corresponding to the axis 610 of FIGS. 6A-6B) so as to define a blunt nose shape to the forward end 620 for improved penetration and patient comfort. The petals 626 are separated by slots 628. The slots 628 are shaped such that the edges of adjacent petals 626 are substantially abutting when the petal assembly 606 is in the fully retracted position. In this manner, the risk of pinching during insertion and withdrawal is reduced. The edges of the petals 626 may also be slightly rounded or otherwise shaped so as to reduce pinching during transition from the dilated configuration to the retracted configuration of the assembly 606. In addition, as shown, the base 630 of each of the slots 628 may be rounded so as to eliminate stress points and potential cracking of the speculum body structure.

As noted above, the petals 626 are turned inwardly at the front end 620 to define a blunt nose shape. Specifically, the petals 626 may turn inwardly over the last 0.25 inches adjacent the tips of the petals 626. At the start of this turn, the front end may have a diameter $d_1$ (FIG. 7A), of no more than about 0.75 inches, for example, about 0.5 inches, in the contracted configuration, and a diameter, $d_2$ (FIG. 6B), of at least 1.5 inches, for example, about 1.75 inches, in the dilated configuration.

In addition, the length of the handle 608 may be between about 3-6 inches, for example, between 4-5 inches. In the illustrated embodiment, the handle is about 4.25 inches. At least the external surface of the handle base 640 may include ribs or other contouring for improved gripping and ergonomics. The overall length of the petal assembly 606 may be between about 4-7 inches, for example, between about 5-6 inches. The illustrated assembly is about 5.5 inches long. The individual blades 626 may be between about 4-5 inches, for example, about 4.5 inches. The illustrated blades have a maximum width of about 0.8-0.9 inches. The thickness of the plastic forming the speculum 600 may be about 0.06-0.15 inches with the thickness varying, e.g., to define flex points.

The overall length of the dilator 604 may be between about 4-7 inches, for example, between about 5-6 inches. The illustrated dilator is about 5.25 inches long. The length from the collar 614 to the front end of the dilator 604 may be between about 4-5 inches, for example, about 4.5 inches. The diameter of the dilator 604 is selected to extend within and expand the blade assembly 606. As noted above, the diameter of the dilator 604 may taper over at least a front section thereof. In the illustrated embodiment, the inside diameter of the dilator 604 at the back end may be about 1.5-1.6 inches and the inside diameter at the front end may be about 1.1-1.2 inches. While the noted dimensions are believed to be suitable to accommodate a large range of patients, the speculum 600 may be provided in other sizes, e.g., for young or small patients (or larger patients).

The petal assembly 606 is connected to the handle 608 via a reinforced central section 634. Hinge portions 632 may be defined where each of the petals 626 meets the central section 634. In the illustrated embodiment, the speculum body 602 is formed from molded plastic. The hinge portion 632 is provided at a narrowed area of each of the petals 626 corresponding to the widened base 630 of the slots 628. The thickness of the plastic may be slightly reduced at the hinge portion 632 to define a fabric hinge. The fabric hinge 632 thus defines the principal location of flexion associated with moving between the dilated and retracted configurations of the assembly 606. More specifically, when the dilator 604 is advanced forwardly so that the forward edge of the dilator 604 extends beyond the hinge portion 632 the dilator 604 begins to press outwardly against the inner surfaces of the petals 626 causing the petals 626 to flex outwardly at the hinge portion 632.

As best seen in FIG. 7D, the handle 608 has a generally U-shaped cross-section defined by a base 640 and sidewalls 642 with an open top 644. A light source receptacle 646 is provided in the interior area of the handle 608. The receptacle 646 is defined by receptacle walls 648 and 650. The walls 648 and 650 are generally parallel and are otherwise configured to receive a light source, such as a penlight, therebetween. In this regard, the walls define a receptacle that has a width, w, and a height, h, selected to securely receive a cylindrical penlight therein. The particular dimensions may be selected to accommodate the desired penlight. In this regard, penlights are typically generally cylindrical in shape and have a diameter selected to securely hold a AAA battery that is often used as a power source. As the AAA battery has a diameter of 0.41 inches, the penlight diameter is generally slightly larger. In the illustrated embodiment, the width, w, of the receptacle and the height, h, of the receptacle are each about 0.4-0.6 inches, for example, about 0.47 inches. The length of the receptacle is about 3-4 inches. The receptacle 646 thus accommodates a variety of penlights that are commercially available including penlights having a diameter of between about 0.45-0.6 inches and a length of between about 3-6 inches.

Each of the walls 648 and 650 further includes continuous or intermittent retaining members 645 for retaining the light source in the receptacle 646. The members 645 are disposed adjacent the upper ends of the walls 648 and 650 away from the base 640 of the handle 608, and extend slightly inwardly toward the center of the receptacle 646 and towards the opposing wall. The plastic walls 648 and 650 can flex sufficiently to allow the light source to be inserted into the receptacle 646 via the open top 644 of the handle 608 such that the light source snaps into place in the receptacle. Alternatively, the light source can be inserted into the receptacle 646 longitudinally by sliding the light source along the length of the receptacle 646.

The open top configuration of the handle 608 and receptacle 646 also allows access to on/off switches of light sources that are located on the rear end of the light source or on a side surface of the light source thus providing additional flexibility in selecting a light source, e.g., to reduce costs. A stop 652 at the forward end of the receptacle 646 defines the forwardmost position of the light source in the receptacle 646. In this manner, the sidewalls 648 and 650 together with the stop 652 ensure proper positioning of the light source so that the light source is aligned as desired with the light directing block 656 as will be described in more detail below. In this regard, the stop 652 extends upwardly from the base 640 of the handle 608 sufficiently to engage and stop the light source but without blocking light from the light source. The illustrated stop 652 has a generally semicircular cross-section and is received within a correspondingly shaped recess 653 formed in the base 640 of the handle 608.

The central section 634 connects the handle 608 to the petal assembly 626, serves as a mounting structure for various elements as will be described below, and receives the dilator 604. Accordingly, the central section 634 will bear substantial forces in operation and needs to be sufficiently strong and stiff. In this regard, the central section 634 may be formed from stronger materials, may be thicker, may be structurally reinforced, or otherwise provided with sufficient strength to perform the noted functions. In the illustrated embodiment, the central section 634 is formed from inner 636 and outer 638 members that collectively thicken and reinforce the central section 634 as well as simplifying manufacturing. The inner member 636 and outer member 638 include complementary tongue and groove connections 657 that allow for convenient sliding interconnection as well as proper alignment and orientation of the members 636 and 638. A groove 658 formed in the inner member 636 receives the ratcheting teeth 618 (FIG. 6A) of the dilator 604 and a recess 660 formed in the groove 658 allows each tooth 618 to register and lock into position. For example, the teeth 618 may be spaced so as to correspond to 0.125-0.25 inch measurements in dilation diameter of the petal assembly 606. The inner member 636 and outer member 638 also have slots formed therein for receiving the light directing block 656 including the dilator retaining guides 654 as will be described in more detail below.

FIG. 7E shows expanded perspective views of the light directing block 656 and the stop 652. Although these components are illustrated as separate pieces, the block 656 and stop 652 may be formed as a single integral unit or both the block 656 and stop 652 may be integrally formed (e.g., molded) as part of the speculum housing 602. In the illustrated implementation, the block 656 is provided as a separate molded plastic piece that is placed in position and fused or bonded to the base of the central portion 634 of the speculum housing 602. Similarly, the illustrated stop 652 is provided as a separate molded plastic piece that can be received in the channel 653 of the handle 608 and can then slide forward in the channel until it abuts the bottom of the block 656. The stop 652 can then be fused or bonded in the desired position.

The illustrated block 656 includes stop retaining guides 654. As will be understood from the description below, the guides 654 extend through a slot formed on the bottom surface of the dilator to guide the sliding motion of the dilator 604 through the petal assembly 606. In addition, the front surfaces of the guides 654 abut against the rear surface of the slot formed in the dilator 604 to define the forwardmost position of the dilator 604 with respect to the petal assembly 606. The forward surface of the guides 654 also abut against the forwardmost end of the slot formed in the dilator 604 to define the fully retracted position of the dilator 604 with respect to the petal assembly 606 and to prevent inadvertent separation of the dilator 604 from the speculum body 602.

When the light source is placed in the receptacle 646 and turned on, light passes above the upper surface of the stop 652 generally in the direction indicated by arrow 657 and is incident on a bottom surface of the guide 656. If desired, a face may be molded into the bottom surface of the guide 656 and oriented normal (or in another desired orientation) to the direction of the light 657. Through processes of refraction, diffusion and/or internal reflection, light exits the forwardmost surfaces of the block 656 and guides 654 generally in the direction indicated by arrow 659. When a standard LED penlight is used as the light source, it has been found that this light, together with other light that illuminates the speculum body 602 and dilator 604, is sufficient to illuminate the procedure site at the front end of the speculum 600. The direction 659 of the exiting light is thus generally aligned with the longitudinal axis of the speculum 600.

Figure 8A:
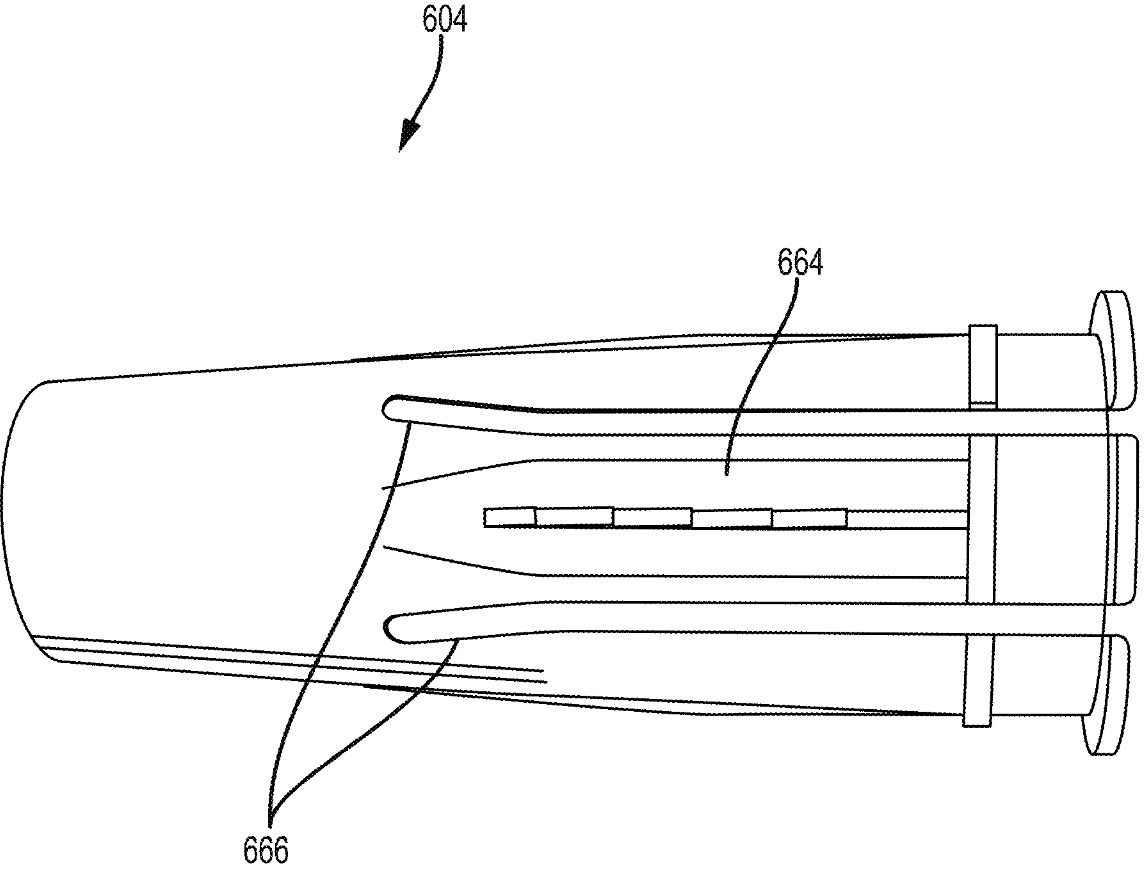
FIG. 8A is a top view of the dilator of the speculum of FIG. 6A.
Figure 8B:
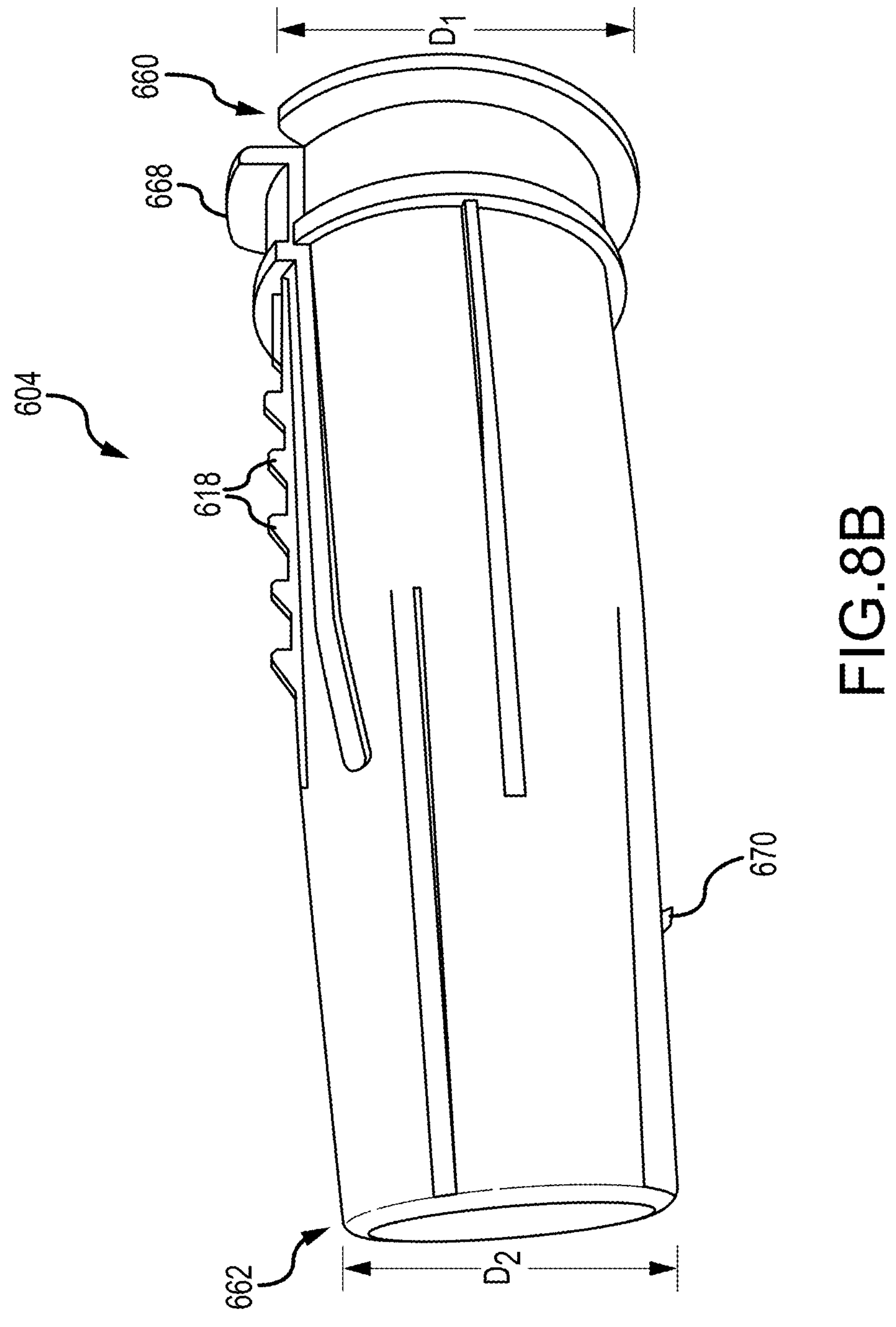
FIG. 8B is a side view of the dilator of the speculum of FIG. 6A.
Figure 8C:
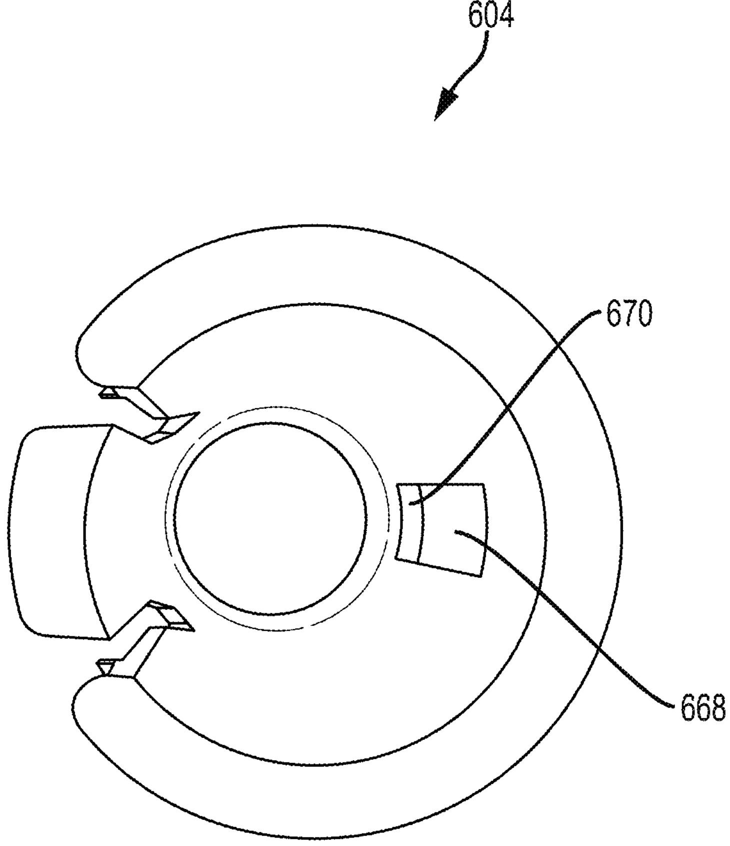
FIG. 8C is a rear view of the dilator of the speculum of FIG. 6A.

FIGS. 8A-8C show various views of the dilator 604. Like the other parts of the speculum 600, the dilator 604 may be formed from molded transparent plastic. As shown, the dilator 604 is slightly tapered from its rear end 662 its forward end 662. This shape better matches the shape of the inner surfaces of the petal assembly 606, facilitates insertion of the dilator 604 into the petal assembly 606 and supports the petal assembly 606 under pressure from the vaginal walls in the dilated configuration. The speculum 600 may be provided in different sizes and shapes in this regard to accommodate different patients, e.g., different ages or different sizes.

As noted above, the dilator 604 includes a thumb flange at the rear end 660 thereof that the user can press to advance the dilator 604. The dilator 604 also includes a collar to limit forward movement of the dilator 604 relative to the speculum body 602. The ratchet teeth 618 are formed on a cantilevered lever defined by slots 666. The cantilevered lever 664 is sufficiently flexible that the lever 664 can be depressed by pressing on the finger grip 668 so as to release the teeth 618 from the recess 660. In this manner, the dilator 604 can be readily withdrawn from the speculum housing 602 and the dilator 604 can be advanced into the speculum body 602 to a desired position without a clicking sound that may be distracting to some patients. The forward ends of the slots 666 flare outwardly slightly from a centerline of the dilator 604 to reduce any structural weakness associated with a single flexion point of the cantilevered portion 664. The bottom surface of the dilator 604 includes an elongate slot 668. The slot 668 receives the guides 654 (FIG. 7F) and allows for controlled sliding of the dilator 604 in relation to the speculum housing 602. A stop 670 is provided at the forward end of the slot 668 to define the fully retracted position of the dilator 604 in relation to the speculum body 602 and to inhibit inadvertent separation of the dilator 604 from the speculum body 602. The stop 670 is sized, in conjunction with the tapered shape of the dilator 604, to enable separation of the dilator 604 from the speculum body 602 when desired and re-insertion thereof.

The inventive speculum as described above is believed to provide a number of performance advantages in relation to conventional specula. For example, the inventive speculum is believed to provide improved visualization and access to the cervix as well as improved support of the vaginal walls so as to prevent collapsing into the field of view. For example, the multiple petal design and the configuration of the forward petal ends tends to allow for improved access.

The inventive speculum also has potential cost advantages. In this regard, the speculum is of simple and inexpensive construction. In addition, the speculum can be used with an off-the-shelf penlight rather than expensive, custom light sources as sometimes required in connection with conventional specula. Moreover, the configuration of the inventive speculum enables use of the speculum even where custom examination tables are not available.

These potential cost advantages, together with certain other cost-effective measures as described below, allow for the possibility of providing a low cost kit for cervical screening and treatment. Such a kit may be provided in one or more containers that include the principal components needed for cervical screening and treatment. For example, components of the kit deemed to be single use components may be provided in a single sealed container such as a sealed plastic bag. Other components that may be deemed suitable for re-use may be provided in a second container or separately. As a practical matter, this may greatly increase the number of women worldwide who are able to receive screening and treatment and has the potential to dramatically reduce deaths from cervical cancer.

Figure 9A:
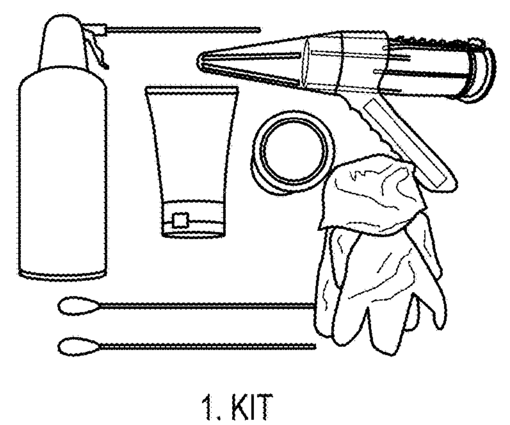
FIGS. 9A-9B show instructions that may be included in a screening and treatment kit including the speculum of FIG. 6A.
Figure 9A:
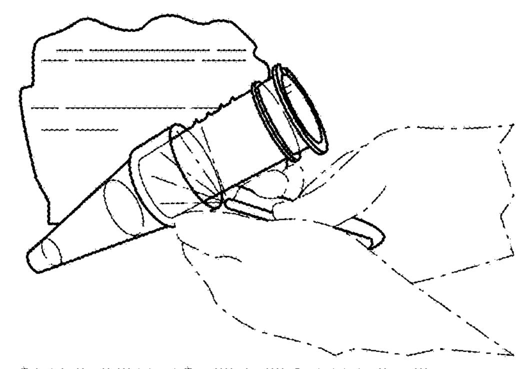
Figure 9A:
Figure 9A:
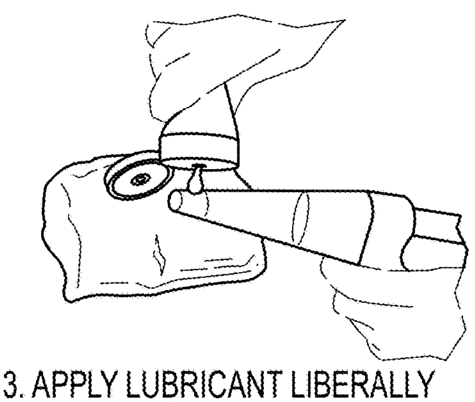
Figure 9A:
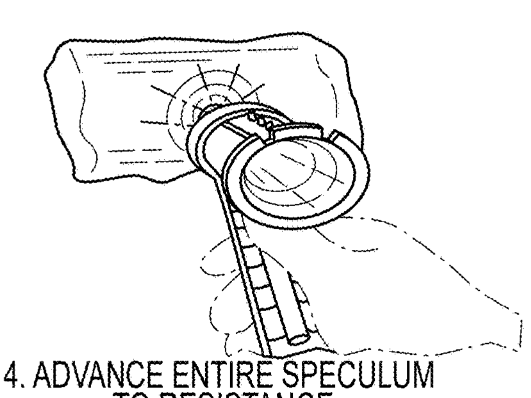
Figure 9A:
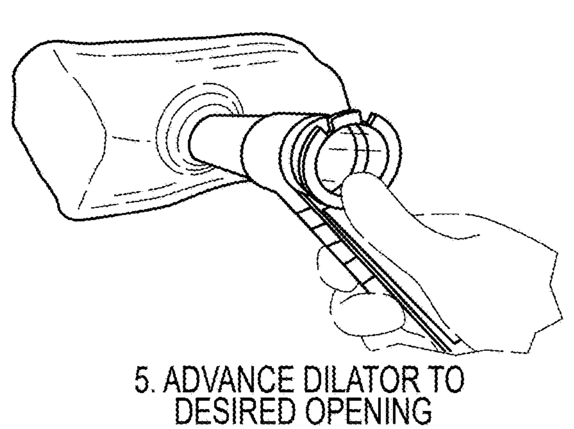
Figure 9A:
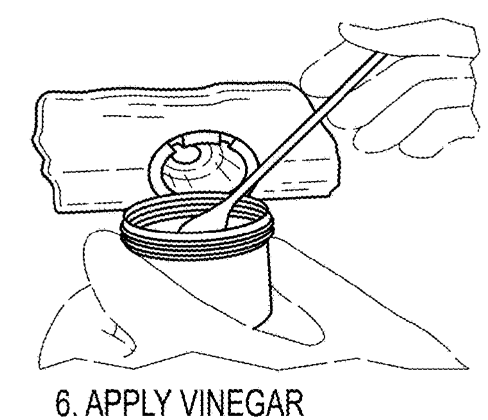
Figure 9B:
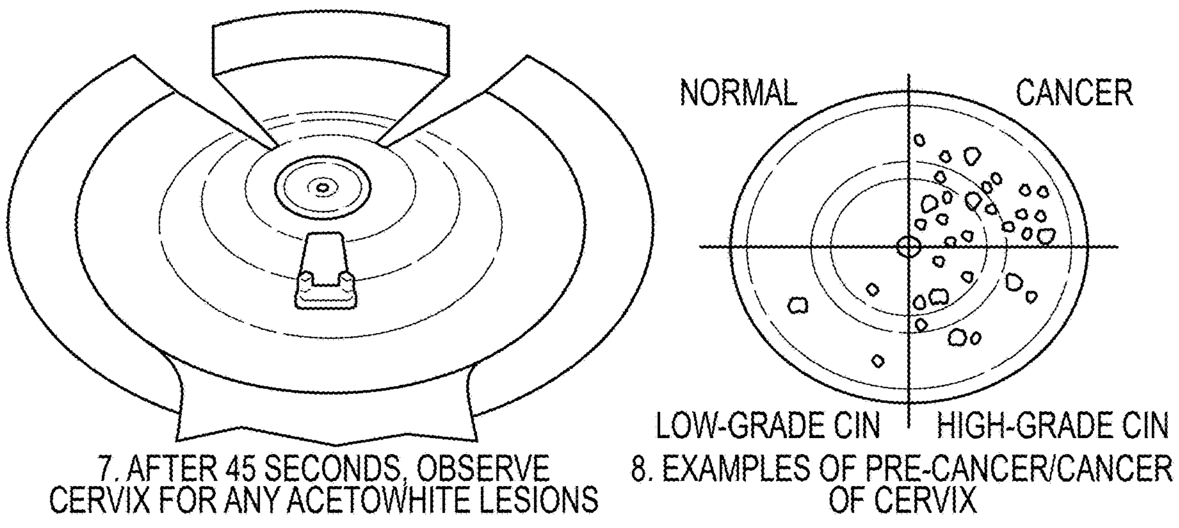
Figure 9B:
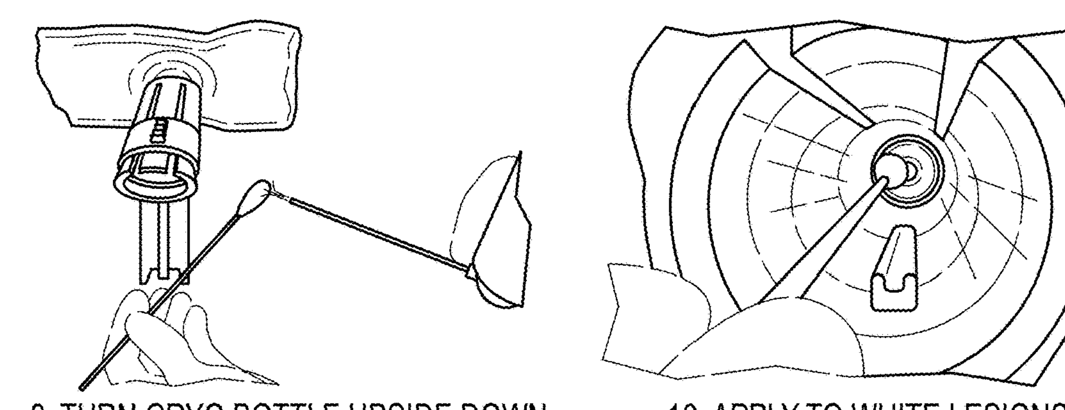
Figure 9B:
Figure 9B:
Figure 9B:
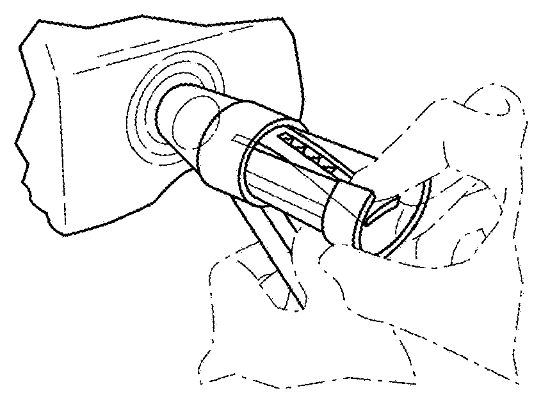
Figure 9B:
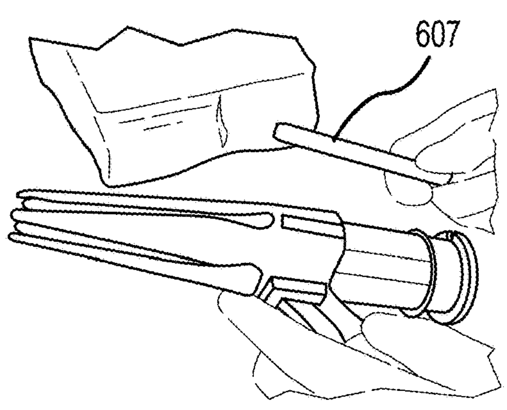

One of the components that may be included in such a kit is a simple set of instructions. An example of what such a set of instructions may look like is shown in FIGS. 9A-9B which also provide a convenient set of illustrations for describing the kit. Referring to FIG. 9A, the first panel of the instructions for screening and treating for cervical cancer shows an example of components that may be included in a kit. The illustrated components include a speculum, surgical gloves, a container of lubricant, a container of a visualization aid, applicators, and a compressed gas container. The use of each of these components will be further explained in the instructions. All of the components shown in the first frame may be included in a single sealed container to provide a relatively inexpensive, self-contained kit for a single procedure. Alternatively, certain components that may be used for more than one procedure, for example, the can of compressed air, the lubricant, and the visualization aid container, may be provided separately such that the kit is defined by multiple kit containers.

As shown in the second panel of the instructions, the user may then snap a penlight (provided as part of the speculum or provided separately as part of the kit) into the handle of the speculum and can turn the penlight on. Panel three instructs the user to apply lubricant to the speculum, e.g., to a latex sleeve extending around the forward end of the petals or directly to the petals. The entire speculum can then be advanced into the patient until resistance is met as shown in panel four. Once the speculum is thus positioned, the user can advance the dilator to dilate the petal assembly to the desired configuration as shown in panel five. Panel six illustrates use of an applicator to apply a visualization agent to the cervix by inserting the applicator through the hollow center of the speculum. Although the instructions indicate that the visualization agent is dilute acetic acid, iodine or other visualization aids are possible.

Referring to FIG. 9B, the instructions proceed with panel seven. Panel seven instructs that, after 45 seconds, the cervix may be observed for any acetowhite lesions. Panel eight provides a depiction of precancerous lesions and cancer of the cervix as well as a normal cervix. Panels nine and ten illustrate a convenient and cost-effective treatment for white lesions. In particular, such lesions may be treated by cryoablation which induces a response in healthy patients that may prevent progression to cancer. In this case, a can of compressed gas is used such as compressed gas cans typically used to remove dust from electronic equipment. Such cans typically include difluoroethane, trifluoroethane or tetrafluoroethene. While these products are marketed as compressed gas containers, the cans generally contain gases that are compressible into liquids. When the can is used in an upright position, high-pressure gas is emitted from the nozzle upon depressing the nozzle and the gas can be precisely directed to the desired location via an elongate tube connected to the nozzle. However, if the can is inverted, a liquid or gas liquid mix may be dispensed. This fluid is dispensed at a very low temperature that, subject to approval or control by a physician where required, may be applied to the lesions for cryoablation treatment.

Thus, panel nine of the instructions directs the user to turn the bottle upside down and spray the tip of the applicator. The applicator can then be inserted through the speculum as shown in panel 10 to apply the cold treatment to the lesions. When treatment is complete, the user can press down on the finger grip of the cantilevered portion of the speculum to withdraw the dilator from the speculum body as shown in panel eleven. The speculum can then be withdrawn from the patient. Panel twelve instructs the user to dispose of the speculum while retaining the penlight for future use.

Mounting Structure

As noted above, a variety of equipment and procedures may be used in conjunction with a speculum. This may involve imaging the cervix, processing images of the cervix for screening or diagnosis, and implementing transvaginal procedures for diagnosis or treatment. In this regard, it may be useful to mount certain equipment or components in relation to the speculum for simplified handling. Such equipment may include, for example, imaging systems or components thereof, medical equipment, or smoke evacuation systems or components thereof as will be described in more detail below.

In certain cases, it is desirable to obtain an image of the subject's cervix. For example, such images may be obtained to provide a baseline image for later comparison or a real-time image for analysis of a condition of interest, e.g., a lesion, discoloration, anomaly or other suspicious cervix condition or other condition. In this regard, a digital image of the subject's cervix may be obtained for digital analysis and/or analysis by a physician, technician, or other analysts. Such analysis may be conducted locally, e.g., on a display screen at the procedure site, or remotely by transmitting one or more images from the procedure site to a remote data terminal, e.g., a phone, tablet computer, desktop computer, or medical image processing system. It will be appreciated that such remote viewing enables convenient access to remote sources and expertise. Moreover, in the case of underserved communities, such remote review can potentially provide access to services that were previously unavailable or impractical.

The present invention facilitates acquisition of digital images as well as transmission of such images via a data network, e.g., the Internet, and remote review and analysis. The invention enables this functionality for modern medical facilities as well as less equipped facilities and even temporary field sites for underserved populations.

Currently, the gold standard for imaging a subject's cervix is colposcope imaging. Colposcopes come in a variety of forms. One common form is typically implemented as multiple pieces of equipment mounted on a mobile cart. The equipment includes a binocular viewer/camera mounted on an arm that can be positioned to view the cervix via the central opening of a conventional, two-blade speculum. A display and a control unit are also mounted on the cart. A user can use the viewer to view the cervix and position the camera for obtaining an image. Images are then displayed in real time on the display. In other cases, the camera component is implemented as a hand-held transvaginal probe that is inserted through the central opening of the conventional, two-related speculum imaging.

These conventional systems for imaging the cervix have a number of drawbacks. First, such imaging requires expensive and bulky equipment that may be impractical for smaller facilities, and especially temporary field sites for underserved populations. Accordingly, some subjects may not be afforded the opportunity for imaging support. In addition, such systems can be cumbersome to operate as they require simultaneous operation of a speculum and a separate imaging system. It may be difficult for an individual user to properly position the speculum and the imaging system while also operating the imaging system to obtain images is desired. Finally, the systems are typically intended for real-time image analysis, at the imaging site, by a physician skilled in such analysis. While this can provide excellent healthcare service for some women, such services are not available to women in many settings.

Accordingly, the present invention includes various embodiments for speculum systems that can interface with imaging systems and data networks for remote image analysis. This includes low-cost, convenient interfaces implemented using, e.g., a smart phone, as well as embodiments that can be implemented in a variety of clinical environments. These speculum systems allow for mounting of imaging system components on a speculum with improved visualization, as described above, so as to enable convenient operation of the speculum system, including by a single user. Moreover, the systems allow for remote analysis by a skilled analyst, with or without image enhancement/digital analysis, to better service women in a variety of clinical/field settings. Finally, the invention makes real-time or nonreal-time image analysis available for many women would otherwise not be able to avail themselves of those services, thus potentially improving health and substantially reducing morbidity and mortality.

FIGS. 10A-10D show a speculum system 1000 in accordance with the present invention. The system 1000 enables a portable imaging/networking device such as a phone 1002 to be mounted on an improved speculum 1012 such as described above. In this manner, users, including users practicing in smaller clinics or temporary field sites, to conveniently obtain high-quality images of a patient's cervix and to transmit those digital images to a remote analyst for analysis, e.g., via email or other networking functionality.

The illustrated system 1000 includes a mounting member 1004, a first adjustable support assembly 1006, a second adjustable support assembly 1008, and an assembly mount 1010. The mounting member 1004 is configured to snap into the handle 1014 of the speculum 1012. As discussed above, the speculum 1012 is formed to receive an illumination source such as a penlight in a channel of the handle 1014 so as to illuminate the subject's cervix. The structure can be used to receive the mounting member 1004. For example, the mounting member 1004 may be a penlight or a dedicated mounting member 1004 having similar dimensions.

The first and second support assemblies 1006 and 1008 are adjustable to receive a variety of devices 1002. One practical implementation is adapted to support a phone 1002 such as any of various commercially available smart phones. It will be appreciated that this is practical for smaller facilities or field sites as smart phones are readily available, images, and enable convenient data network access. In this regard, the phone can transmit digital images to a remote analyst using email or using an application loaded on the phone for uploading images directly to a facility of the analyst or a platform such as a cloud-based platform as will be discussed in more detail below.

The support assemblies 1006 and 1008 may be adjustable to securely hold smart phones of a variety of dimensions. In addition, the assemblies 1006 and 1008 may allow for vertical positioning of the smart phone so that a camera of the smart phone is aligned with an axis of the speculum 1012 to obtain an image of the subject's cervix. In this regard, the assembly 1006 may include slides or other telescoping mechanisms to enable longitudinal expansion and contraction to engage the sides of the phone 1002. Similarly, the assembly 1008 may include slides or other telescoping mechanisms to allow the mechanism 1008 to be vertically raised or lowered to position the camera of the device 1002 as desired.

Figure 10A:
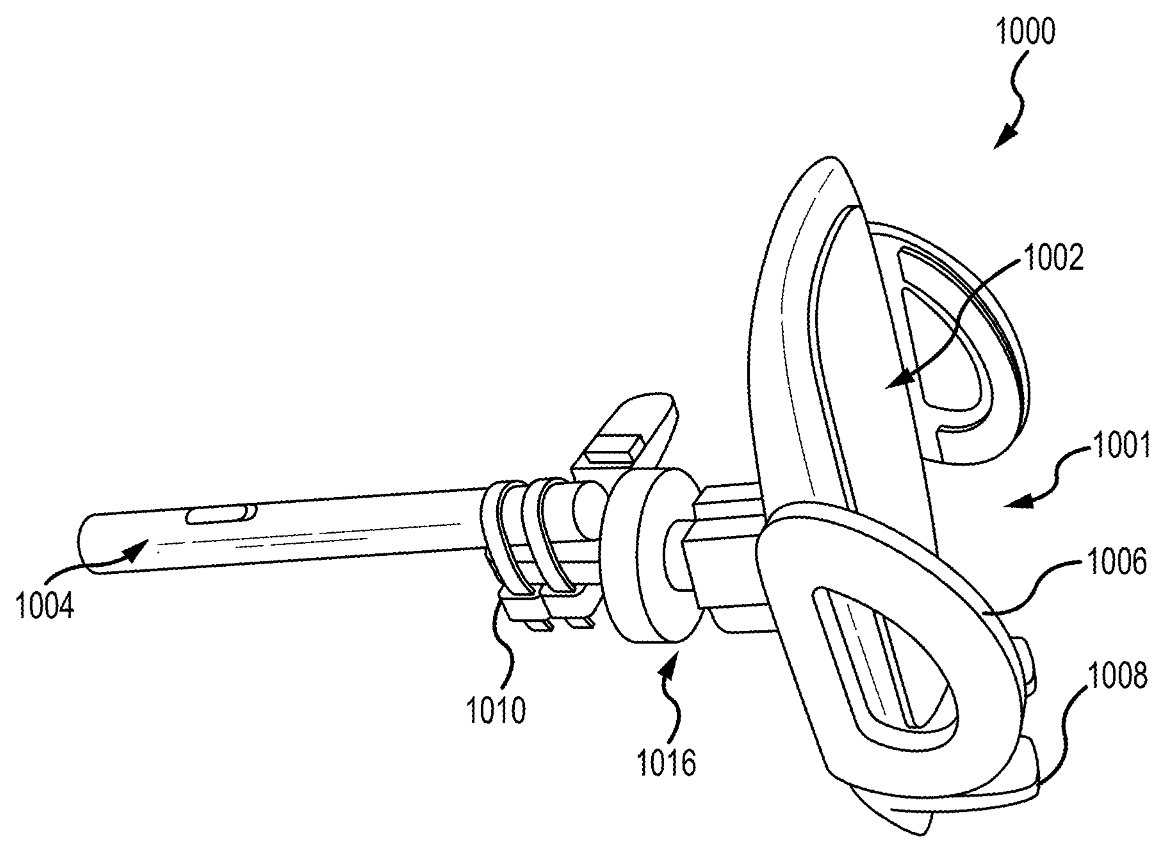
FIGS. 10A-10D show an embodiment of a speculum system in accordance with the present invention including an imaging/data device mount.
Figure 10B:
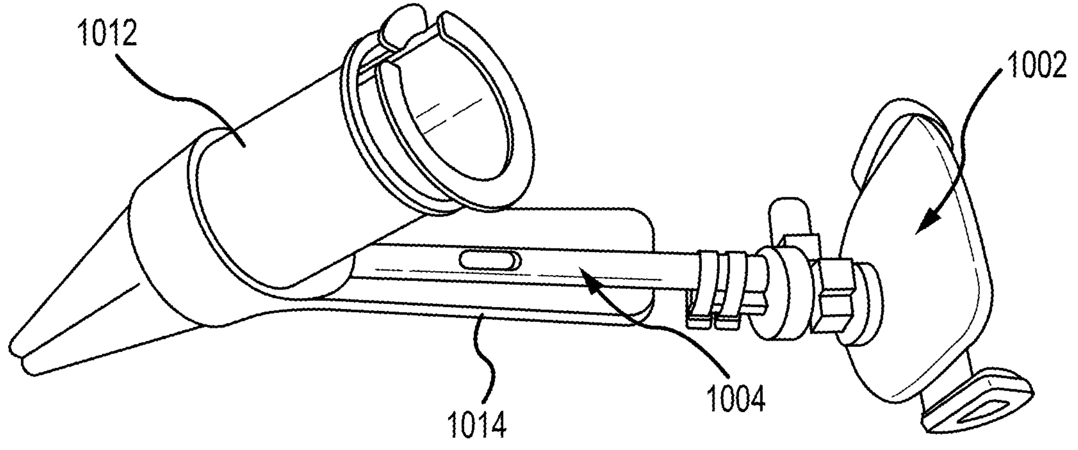
Figure 10C:
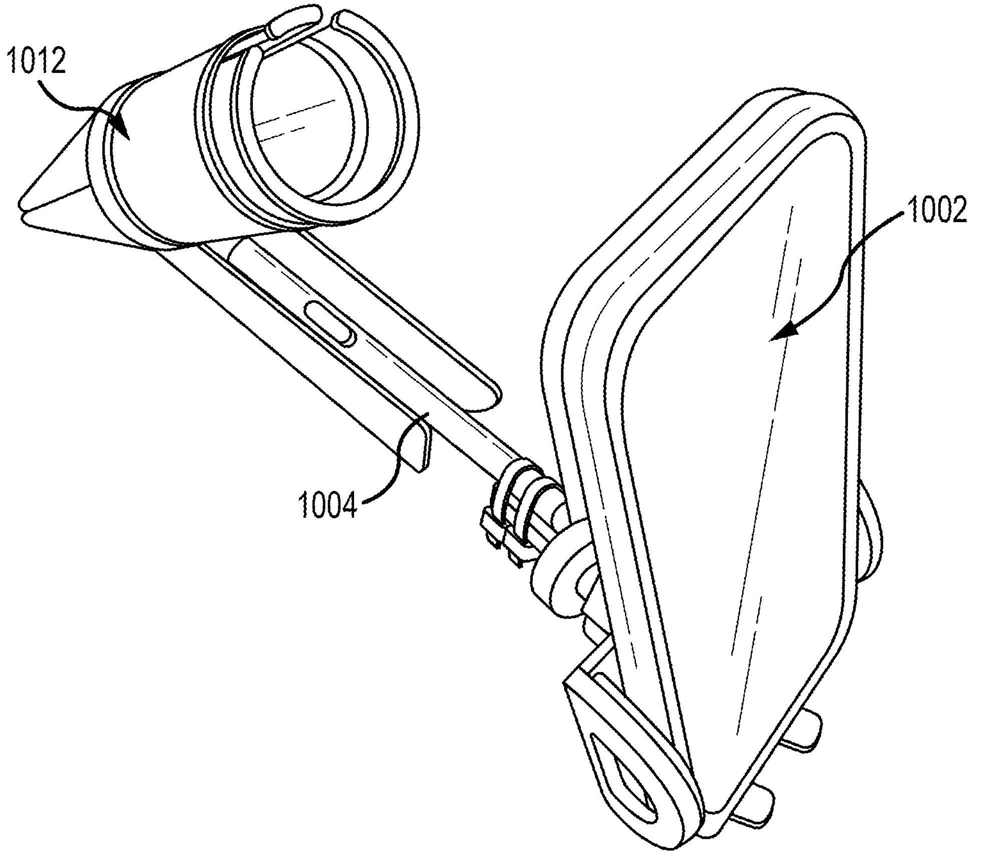
Figure 10D:
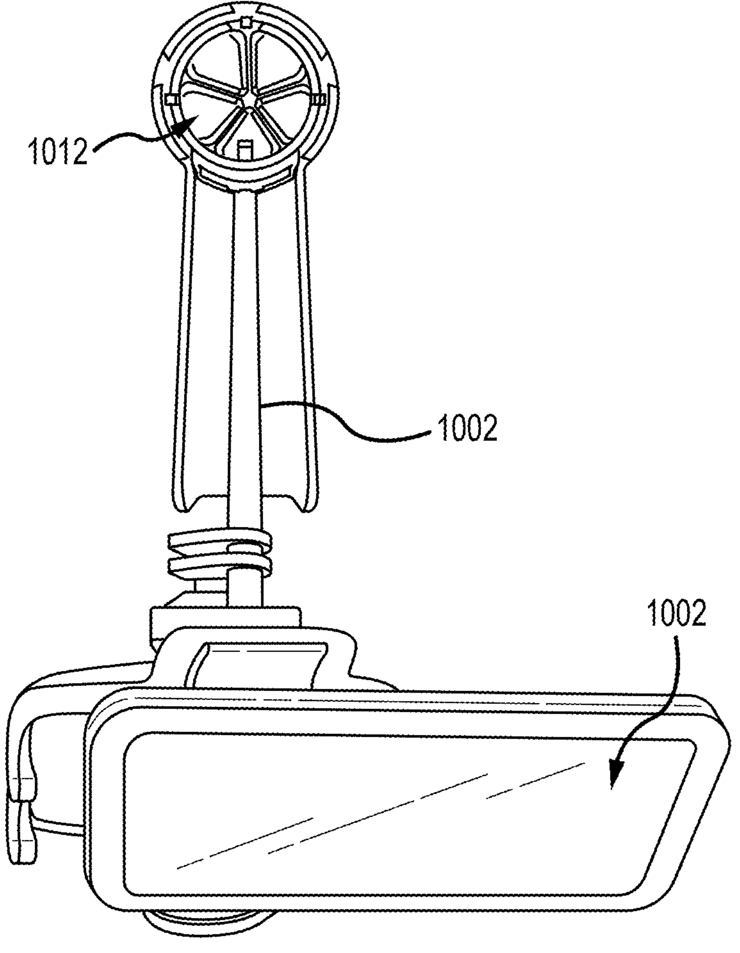

The illustrated system 1000 also includes a mount 1010 for mounting the device support assembly 1001 on the mount member 1004. In the illustrated embodiment, the assembly 1001 is substantially permanently mounted on the member 1004 using bands, zip ties, or other mounting structure. Alternatively, the assembly 1001 may be removably mounted on the member 1004 via a snapping plastic grip or similar mechanism. The assembly 1001 may further include an adjustable joint 1016 for allowing the assembly 1001 to be movable so as to move the device 1002 to a desired position and angle. In this regard, joint 1016 may rotate or pivot and translate or allow for linear motion of the assemblies 1006 and 1008 relative to the mount 1004. Moreover, as shown in FIG. 10D, the joint 1016 also allows the device 1002 two be rotated to a horizontal position to be out of the way, for example, to allow a user to view the cervix or access the cervix for a medical procedure such as cryoablation or sampling.

Figure 11A:
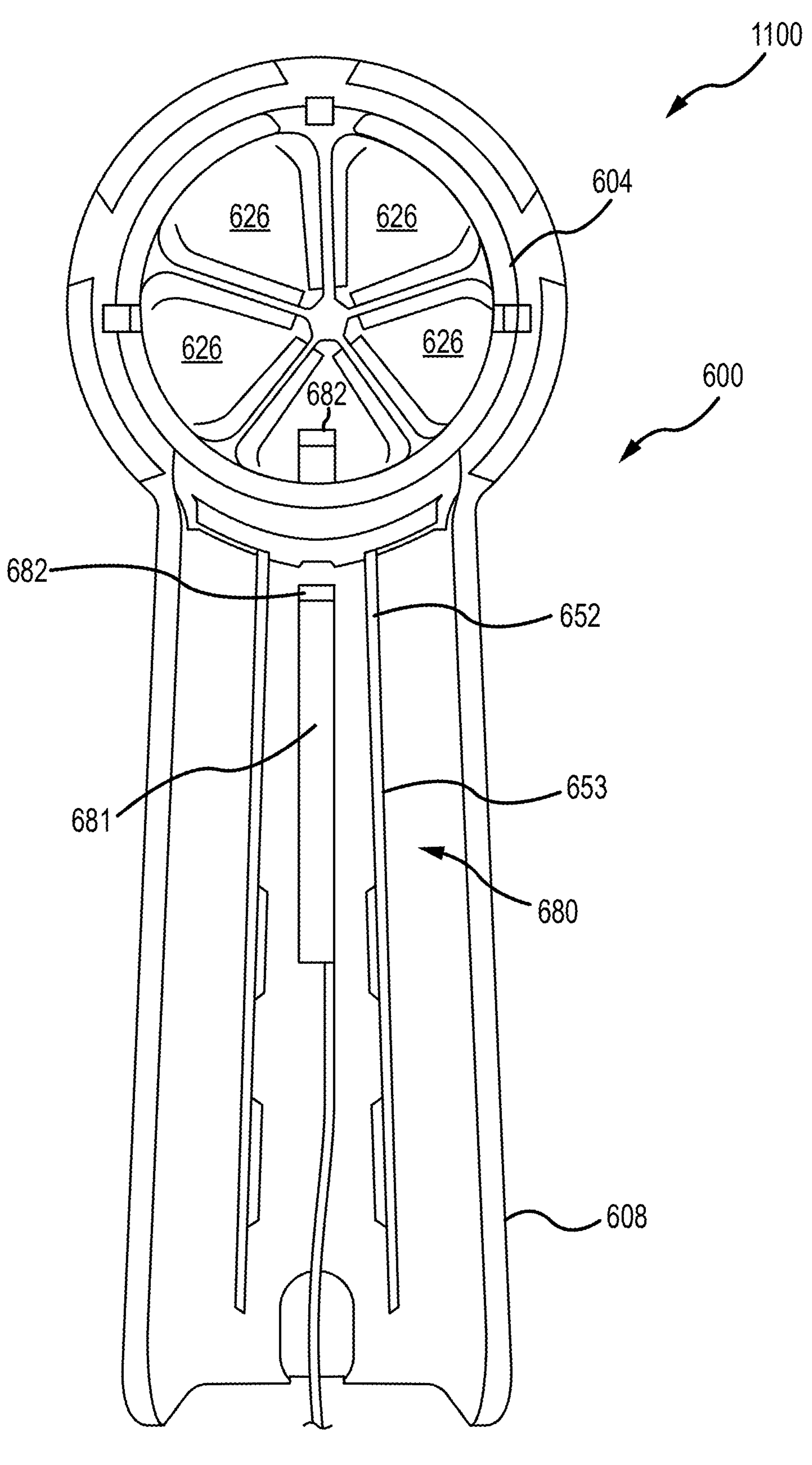
FIGS. 11A-11C show another embodiment of a speculum system in accordance with the present invention including an imaging/data device mount.
Figure 11B:
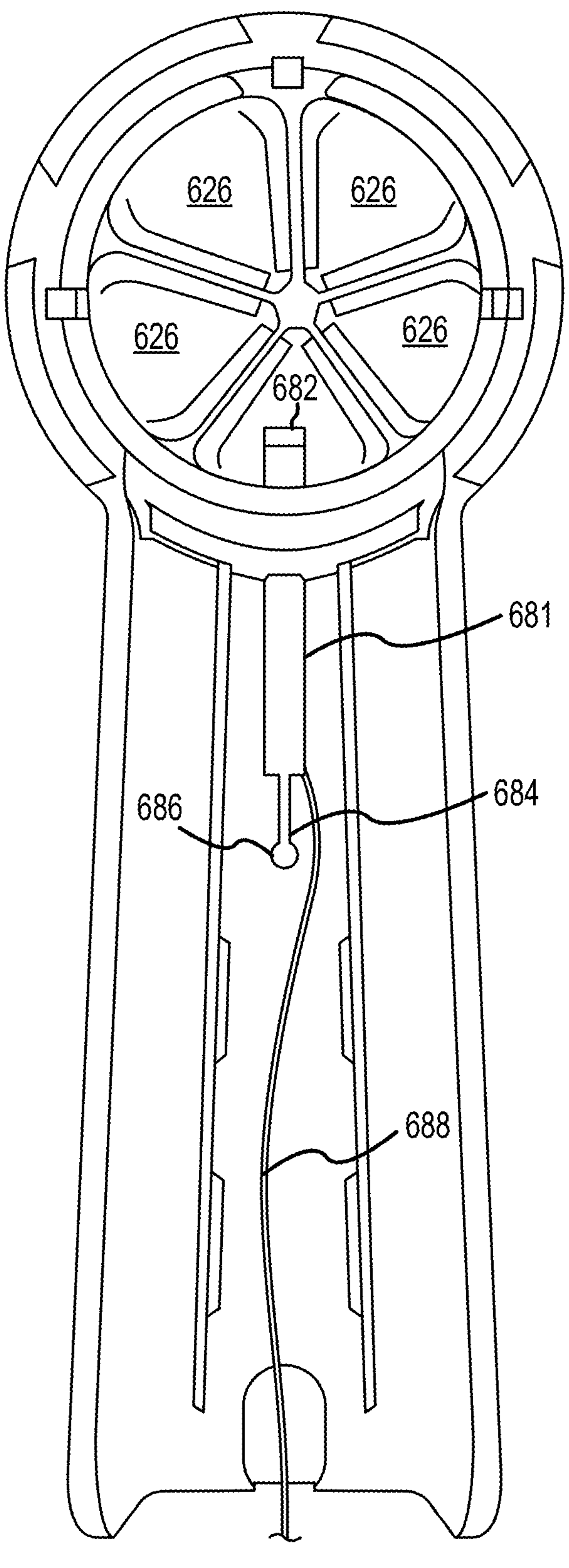
Figure 11C:
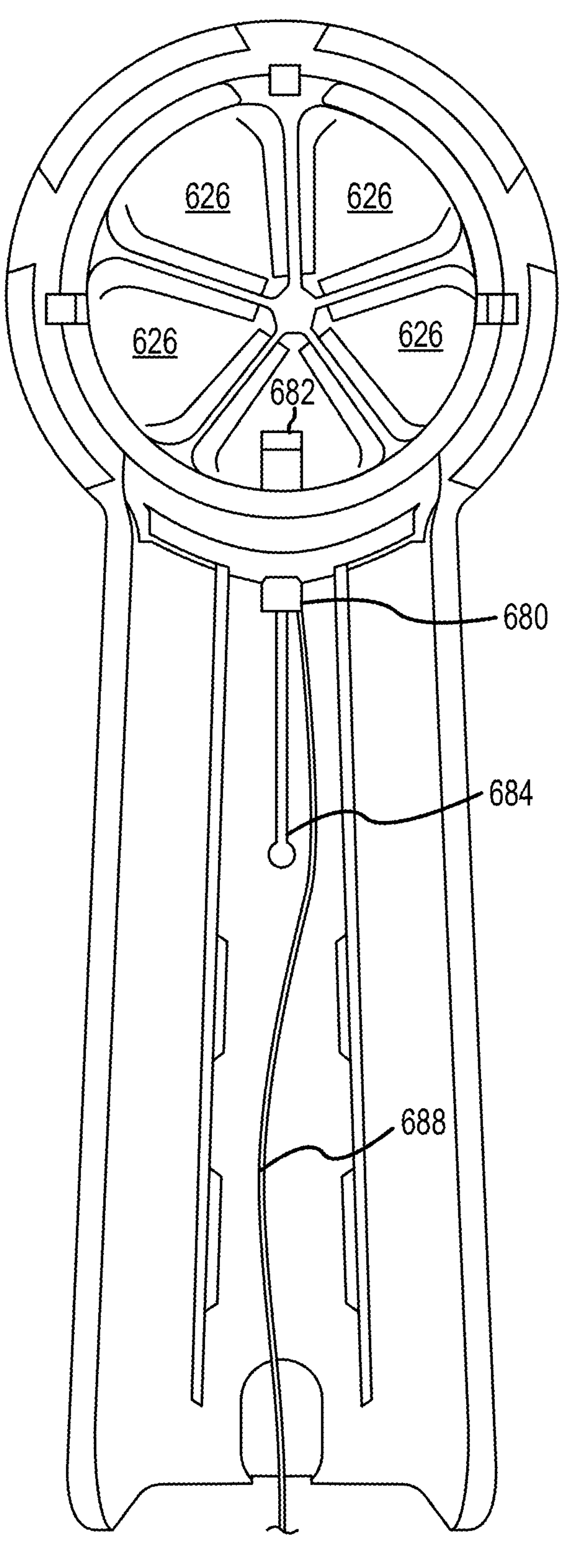

FIGS. 11A-11C show another embodiment of a speculum system 1100 in accordance with the present invention. The system 1100 includes a speculum 600 that is generally similar to the speculum described above in connection with FIGS. 6A-6B and corresponding elements identified by the same reference numerals as in those FIGS. However, the illustrated system 1100 further includes a removable imaging system 680 that can be movably mounted on the handle 608. As shown, the imaging system 680 includes an elongate body 681 and a digital imaging detector 682. Alternatively, the system 680 may include a fiber optic element connected to a remote detector. Although not shown, the system 680 may further include lenses, filters, fiber optic reducers, or other imaging elements. The body 681 is movably mounted in an elongate slot 684 formed in the handle 608. For example, the body 681 may include one or more protrusions that are received in an opening 686 at an end of the slot 684. In this manner, the body 681 and detector 682 can move longitudinally within the slot 684.

FIGS. 11A-11C show the body in a fully withdrawn position (FIG. 11A), for example, to avoid interfering with viewing or performing medical procedures on the patient's cervix, a partially inserted position (FIG. 11B), and a fully inserted position (FIG. 11C), for example, for obtaining images of the subject's cervix. It will be appreciated that the body 681 can extend through an opening formed in the body of the speculum 600 and dilator 604. For example, such openings may be circular, rectangular, or, in the case of the dilator 604, an elongate slot to permit movement of the dilator 604 in relation to the body of the speculum 600. The illustrated system 1100 further includes a cord 688 for supplying power to the imaging system and communicating with a remote system for image processing. It will be appreciated that the image information may be processed locally or remotely via a data network as discussed in more detail below.

Figure 12A:
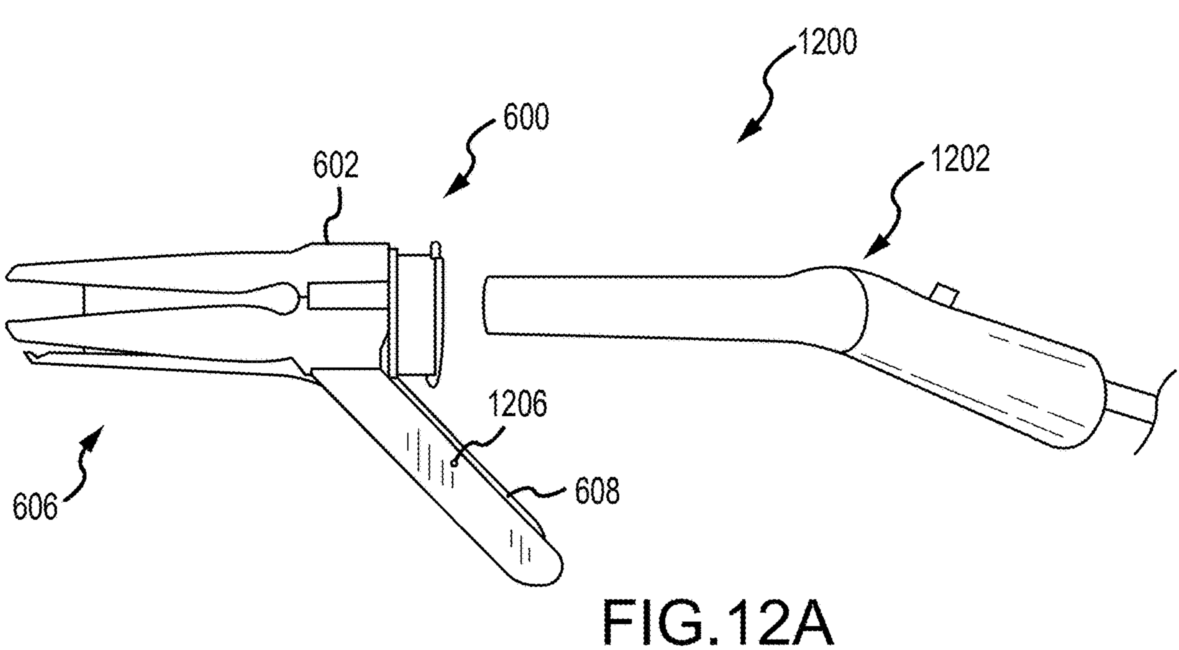
FIGS. 12A-12B show a still further embodiment of a speculum system in accordance with the present invention including an imaging/data device mount.
Figure 12B:
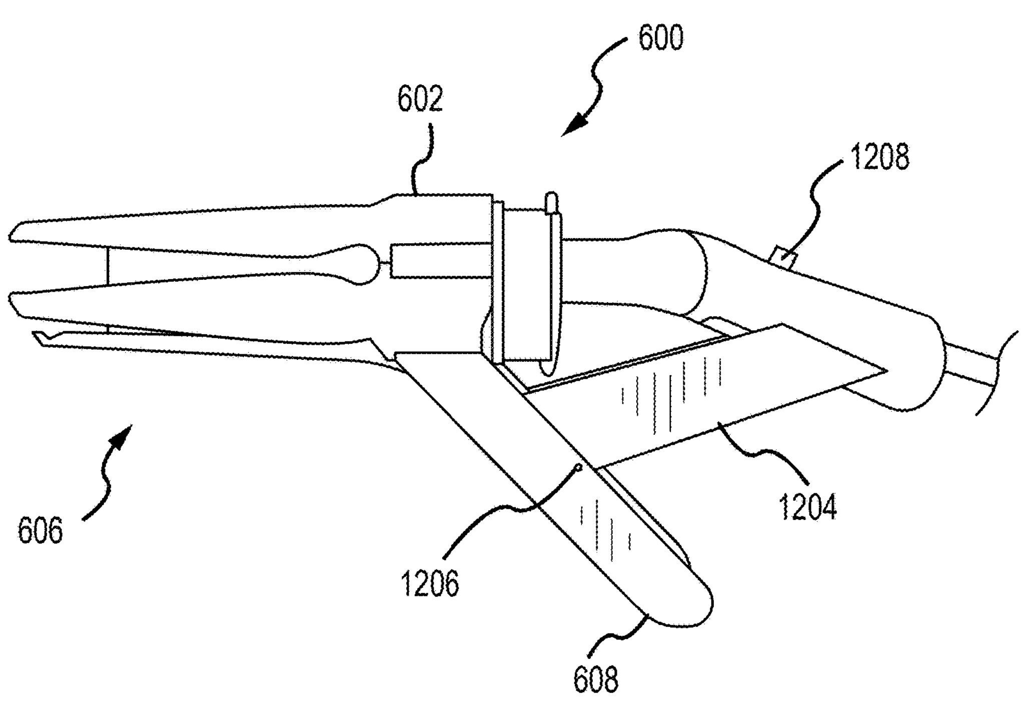

FIGS. 12A-12B show a further embodiment of a speculum system 1200 in accordance with the present invention. The illustrated system 1200 includes a speculum 600, such as described above in connection with FIGS. 6A-6B, and a colposcope hand-held imaging device 1202. As shown in FIG. 12B, the device 1202 can be longitudinally inserted into the central opening of the speculum 600 to obtain images of the subject's cervix. In this regard, the illustrated speculum 600 includes a device support 1204 that is hingedly mounted on the handle 608 of the speculum 600 at pivot 1206. In this manner, the support 1204 is movable between a retracted position, where the support 1204 is withdrawn into the handle 608 and a deployed position, as shown in FIG. 12B, where the support 1204 supports the body of the device 1202. The support 1204 may be securely maintained in the deployed position by a ratchet or locking mechanism among other possibilities. In addition, if desired, a flexible annular support ring may be mounted on a forward portion of the device 1202 to further secure the device 1202 within the dilator of the speculum 600. It will be appreciated that the system 1200 thus allows a user to conveniently position both the speculum 600 and the device 1202 using the handle 608. The user's other hand is thus available to operate light and camera controls 1208 on the device 1202 or for other operations.

Figure 13:
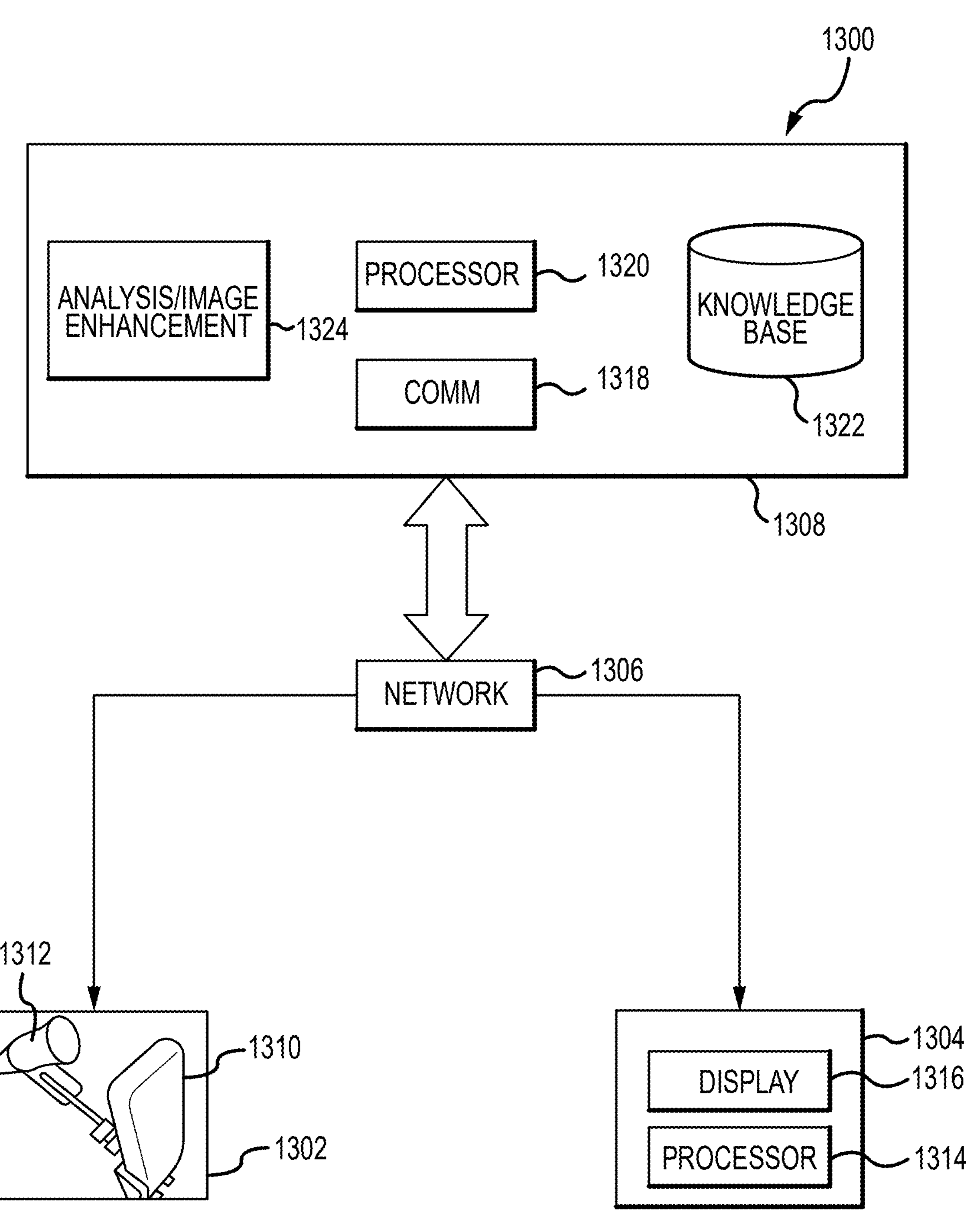
FIG. 13 shows a speculum system in accordance with the present invention including a data network architecture.

FIG. 13 shows an image processing system 1300 in accordance with the present invention. The illustrated system includes an imaging site 1302, a remote analysis site 1304, a network 1306, and an optional processing platform 1308. At the imaging site, the user can operate a speculum system including a speculum 1312 and a device 1310, as described above, for obtaining one or more images of a subject's cervix. The resulting digital images can be transmitted to the remote analysis site 1304 via the network 1306. For example, the network 1306 may include a wireless network and a data network such as the Internet. In one implementation, the user can attach one or more images to an email and send the email to the remote analysis site 1304. Alternatively, a user may download an application of a processing system in accordance with the present invention to the device 1310. The application may work in coordination with logic resident on a processor 1314 of the remote analysis site 1304 or resident on the processing platform 1308. For example, the application on the device 1310 may communicate with such logic via an API defining messaging protocols, data fields, and formats among other things. In this manner, the digital images or enhanced versions thereof may be displayed on the display 1316 at the remote analysis site 1304 for review by an analyst. The analyst can then provide feedback to the user at the imaging site 1302 based on analysis of the images. Such feedback may be provided, for example, by phone, text messaging, email, messaging interfaces of the application running on the device 1310, or other means.

Optionally, images from the imaging site 1302 and other imaging sites may be processed by a processing platform 1308. For example, the processing platform 1308 may be a cloud-based processing platform and may be embodied in one or more machines at a single location or geographically distributed. The illustrated platform 1308 includes a communications module 1318, a processor 1320, a knowledge base 1322 and an image analysis/enhancement module 1324. The communications module 1318 manages communications with the imaging site 1302 and remote analysis site 1304, among others, and may perform functionality including formatting messages, extracting data fields from messages, data feature identification and extraction, and the like.

The module 1324 is operative to process and enhance imaging information from the site 1302. For example, the functionality implemented by the module 1324 may include contrast enhancement, resolution enhancement, identifying and analyzing image features or other areas of interest, annotating the image in relation to areas of interests or other information, and comparison of image features to known features and conditions as stored in a knowledge base 1322. For example, the module 1324 may implement artificial intelligence or machine learning to progressively improve identification of areas of interest within an image and correlation of image features to known or learned medical conditions.

The knowledge base 1322 stores knowledge learned from analysis of images. This may include information concerning features, values, variations, correlations involving subject demographic or medical information, or the like. In this regard, the platform 1308 may receive or access various sources of demographic information, medical records, medical literature, and other information to assist in such analysis. The processor 1320 controls operation of the modules 1318, 1324, and 1322. It will be appreciated that such a cloud-based platform 1308 may have access, over time, to a large volume of imaging information regarding cervical examination so as to develop substantial expertise in identification of potential missions of interest. In some cases, this may enable analysis of conditions at the imaging site 1302 without requiring the expertise of an analyst at a remote platform 1304.

Certain medical procedures may involve ablation, cauterization, or other treatments that may generate smoke at the procedure site. For example, in connection with a cervical examination, a physician may perform a LEEP (Loop Electrosurgical Excisional Procedure) to treat pre-cancers and cancers of the cervix. In such procedures, the wire filament of the electrosurgical device may be heated to about 2000 degrees Fahrenheit and may generate considerable smoke that can obstruct viewing of the surgical site if not removed, potentially resulting in unnecessary tissue burns or resulting in failure to fully remove the diseased tissue. While expensive and bulky smoke evacuators have been used for this purpose in clinical settings, it is envisioned that a compact, and optionally battery-operated fan/vacuum unit may be employed for this purpose in accordance with the present invention. In this regard, the battery and fans of a conventional hand-vac system, modified to interface with an evacuation tube as described below, may be sufficient for many applications.

Figure 14A:
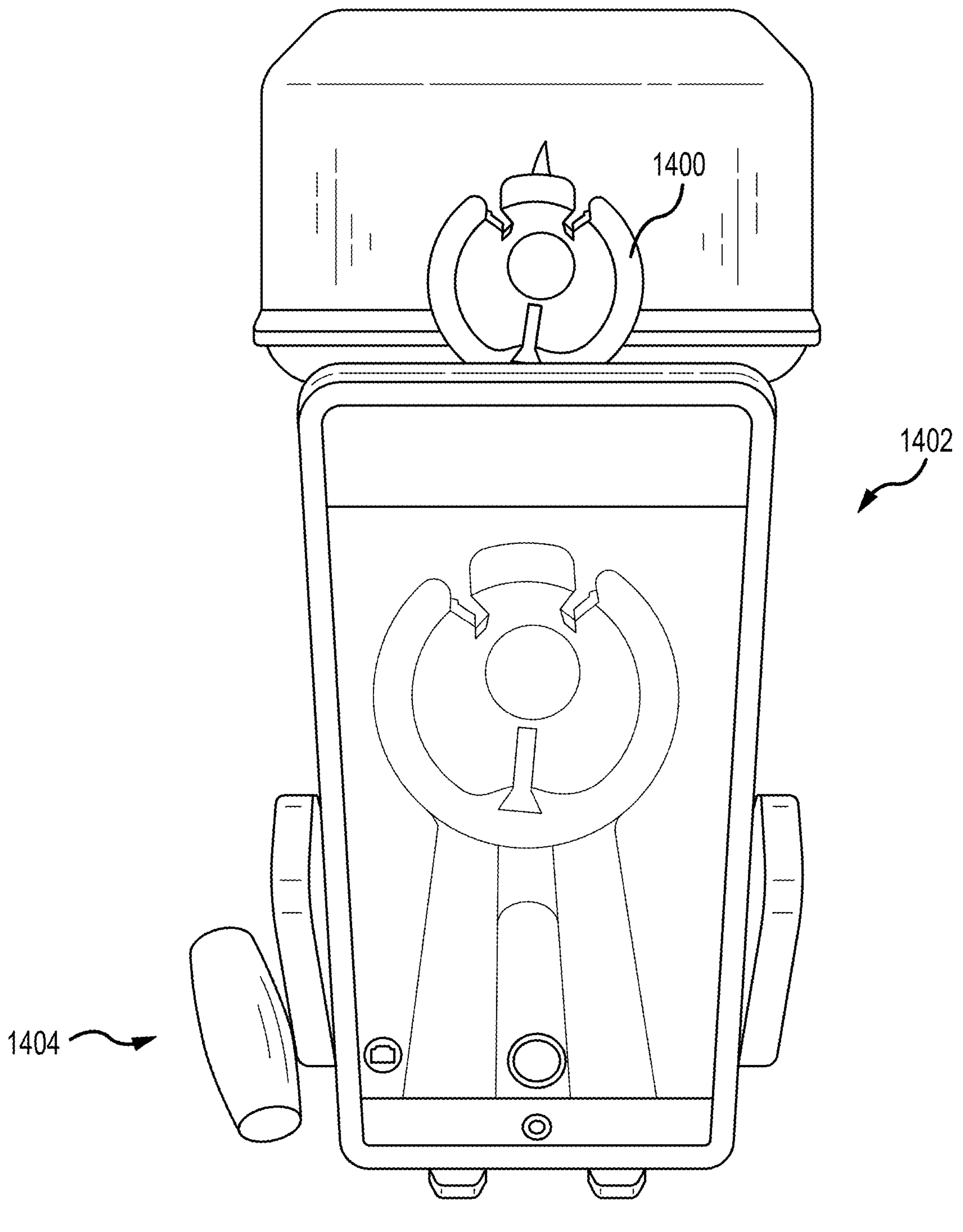
FIGS. 14A-14C show a speculum system in accordance with the present invention including a smoke evacuation tube mount.
Figure 14B:
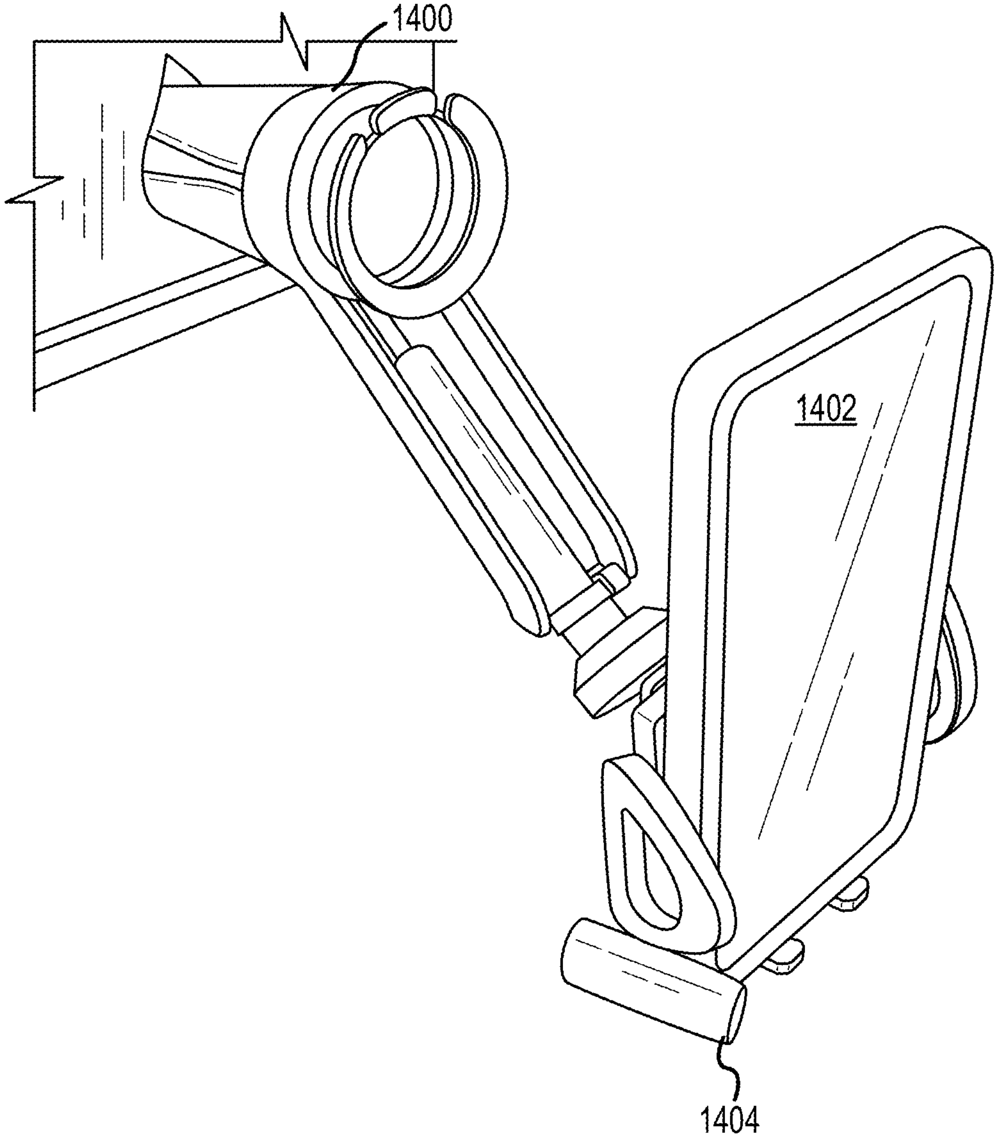
Figure 14C:
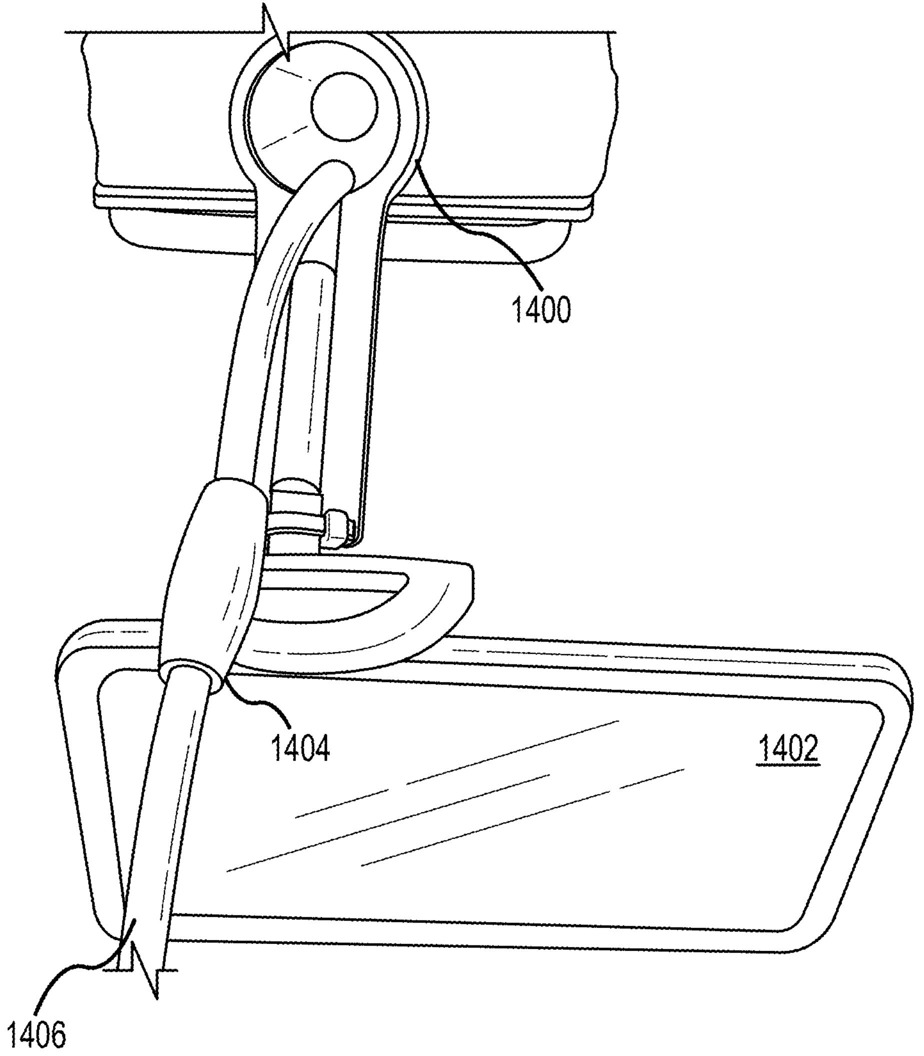

FIGS. 14A-14C show a speculum system in accordance with the present invention including a mount for holding a smoke evacuation hose. Specifically, the system includes a speculum 1400 and an imaging/data device 1402 as generally described above in connection with FIGS. 10A-10D. The illustrated system further includes a smoke evacuation tube mount 1404 such as a ring or tube segment for securely receiving a smoke evacuation tube 1406 therein as shown in FIG. 14C. The evacuation tube 1406 has one end extending into the internal cavity the speculum 1400 so as to draw smoke from the procedure site. Although the tube mount 1404 is shown as being attached to the imaging/data device mount, it will be appreciated that the tube mount 1404 may alternatively or additionally be disposed on the handle of the speculum, the dilator of the speculum, or another location. For example, a first tube mount element may be provided on the imaging/data device mount as shown and a second tube mount element such as a molded tube support ring may be provided on the dilator of the spectrum to secure the end of the tube.

In the illustrated embodiment, the tube mount 1404 is positioned so as to support the smoke evacuation tube 1406 in alignment with the speculum when the imaging/data device mount is rotated away from the speculum opening as shown. The imaging/data device mount and smoke evacuation tube mount may be provided as part of a speculum system kit as described above in connection with FIGS. 9A-9B. It will be appreciated that the other end of the tube 1406 may be attached to a fan, vacuum device, or other device for drawing air and smoke through the tube away from the procedure site. Such a device may include a power source. For some applications, it may be convenient to provide a battery-operated fan or vacuum device, e.g., to eliminate power cords from the procedure site or where grid power is unavailable or inconvenient to access.

Figure 15:
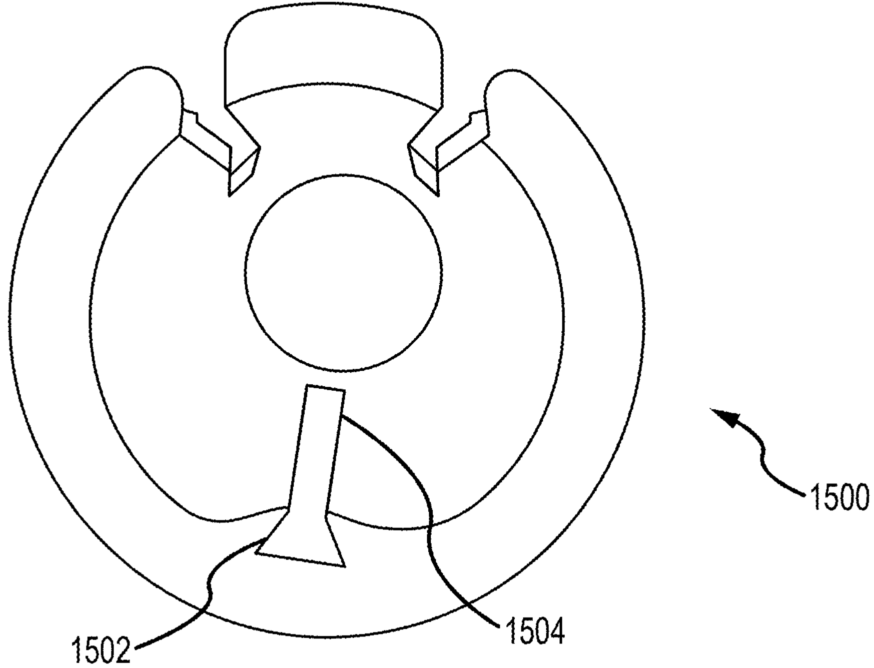
FIG. 15 shows a speculum dilator with an accessory channel in accordance with the present invention.
Figure 16B:
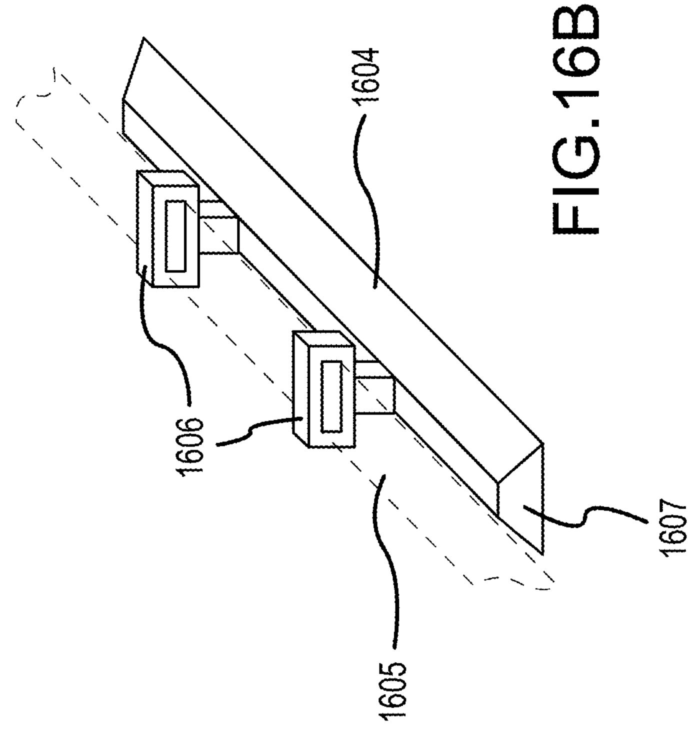
FIGS. 16A-16B show accessory mounts for a speculum system in accordance with the present invention.
Figure 16A:
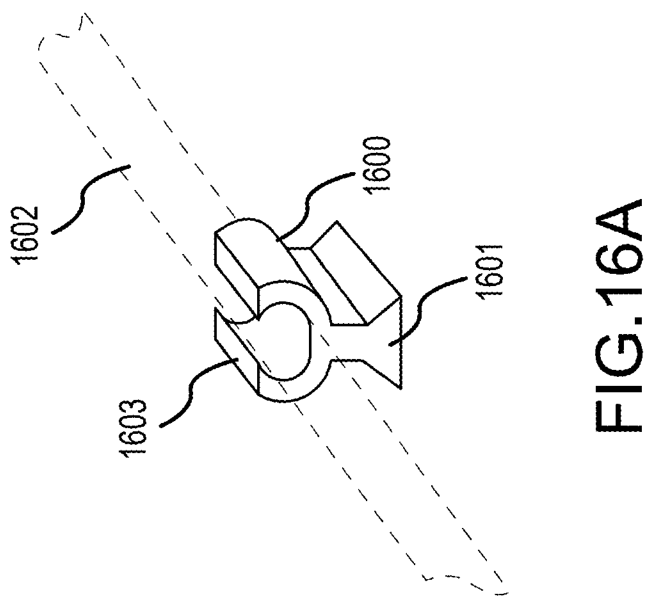

In certain situations, it may be desired to mount accessories on the speculum system. For example, it may be desired to mount a smoke evacuation tube, an imaging system element, or an electrosurgical instrument guide/rest on the speculum. Mounting structure may be provided on the dilator of the speculum for this purpose. In this regard, FIG. 15 shows a dilator 1500 including a notch 1502 and a longitudinal channel 1504 for receiving an accessory mount. FIGS. 16A-16B show examples of accessory mounts 1600 and 1604 that may be received within the notch 1502 and longitudinal channel 1504. Specifically, the mount 1600 includes a base 1601, dimensioned to be received within the notch 1502 of the dilator 1500, and a "C" shaped tube receptacle for receiving a smoke evacuation tube 1602. The mount 1604 includes an elongate base 1607, dimensioned to be received within the notch 1502 of the dilator 1500, and one or more receptacles 1606 for receiving an imaging element 1605 of an imaging system. The imaging element 1605 can move longitudinally through the receptacle(s) 1606 so that an imaging detector at the end of the element 1605 is positioned at a desired location in relation to the subject. It will be appreciated that other mounts for other equipment may be provided, for example, as part of a kit as described above.

The foregoing description of the present invention has been presented for the purpose of illustration and description. Furthermore, the description is not intended to limit the invention to the form disclosed herein. Consequently, variations and modifications commensurate with the above teachings, and skill and knowledge of the relevant art are within the scope of the present invention. The embodiments described herein above are further intended to explain best modes known of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed:

1. A speculum apparatus, comprising:

a speculum including a distal portion, for positioning within a subject to dilate the subject so as to provide an enlarged opening to the subject's cervix in alignment with a speculum axis of said speculum, and a proximal portion, said proximal portion including an elongate handle for gripping, said elongate handle extending from said proximal portion relative to a transverse axis that is transverse to said speculum axis;

an imaging system for obtaining one or more images of said subject's cervix via said enlarged opening; and a data network system, operatively associated with said imaging system, for transmitting said images, via a data network, to a remote data terminal for analysis;

wherein said speculum includes a mount for receiving structure of said imaging system such that an imaging element of said imaging system is in an imaging position proximate to said proximal portion of said speculum for imaging said subject's cervix, said mount enabling movement between a first position, corresponding to a first location in relation to said transverse axis, for imaging said subject's cervix and a second position, corresponding to a second location in relation to said transverse axis, where said imaging system is disposed away from said enlarged opening so as to facilitate access to said subject's cervix, wherein, in said second position, said imaging element is separated from said speculum axis of said speculum by a first distance that is greater than any distance between said imaging element and said speculum axis in said imaging position.

2. The apparatus of claim 1, wherein said imaging system is embodied in a phone and said mount comprises an assembly for supporting said phone.

3. The apparatus of claim 2, wherein said assembly is disposed on said handle of said speculum.

4. The apparatus of claim 2, wherein said assembly is movably interconnected to said handle of said speculum.

5. The apparatus of claim 4, wherein said assembly is movable to enable positioning of said imaging element for imaging said subject's cervix.

6. The apparatus of claim 4, wherein said assembly enables angular movement of said imaging element.

7. The apparatus of claim 4, wherein said assembly enables translational movement of said imaging element.

8. The apparatus of claim 1, wherein said structure of said imaging system comprises at least one of an imaging detector and an optical element for use in transmitting imaging information from an optical interface to an imaging detector.

9. A speculum apparatus, comprising:

a speculum including a distal portion, for positioning within a subject to dilate the subject so as to provide an enlarged opening to the subject's cervix in alignment with a speculum axis of said speculum, and a proximal portion, said proximal portion including an elongate handle for gripping said elongate handle extending from said proximal portion relative to a transverse axis that is transverse to said speculum axis;

a mounting system for mounting an imaging element of an imaging system on said speculum in an imaging position for obtaining one or more images of said subject's cervix via said enlarged opening, said mounting system enabling movement between a first position, corresponding to a first location in relation to said transverse axis, for imaging said subject's cervix and a second position, corresponding to a second location in relation to said transverse axis, wherein said imaging element is disposed away from said enlarged opening so as to facilitate access to said subject's cervix, wherein, in said second position, said imaging element is separated from said speculum axis of said speculum by a first distance that is greater than any distance between said imaging element and said speculum axis in said imaging position.

* * * * *